US008998802B2

(12) United States Patent
Gono et al.

(10) Patent No.: US 8,998,802 B2
(45) Date of Patent: Apr. 7, 2015

(54) ENDOSCOPE, ENDOSCOPIC APPARATUS, AND EXAMINATION METHOD USING ENDOSCOPE

(75) Inventors: Kazuhiro Gono, Sagamihara (JP); Takaaki Gono, Hachioji (JP); Naruto Shinkai, Kawasaki (JP)

(73) Assignee: Olympus Medical Systems Corp., Tokyo (JP)

( * ) Notice: Subject to any disclaimer, the term of this patent is extended or adjusted under 35 U.S.C. 154(b) by 2248 days.

(21) Appl. No.: 11/439,815

(22) Filed: May 24, 2006

(65) Prior Publication Data

US 2007/0276185 A1    Nov. 29, 2007

(51) Int. Cl.
| | |
|---|---|
| A61B 1/12 | (2006.01) |
| A61B 1/06 | (2006.01) |
| A61B 18/04 | (2006.01) |
| G01J 3/00 | (2006.01) |
| A61B 5/026 | (2006.01) |
| A61B 1/00 | (2006.01) |
| A61B 1/015 | (2006.01) |
| A61N 5/06 | (2006.01) |

(52) U.S. Cl.
CPC .............. *A61B 5/0261* (2013.01); *A61B 1/0008* (2013.01); *A61B 1/015* (2013.01); *A61B 1/0638* (2013.01); *A61B 1/12* (2013.01); *A61N 2005/066* (2013.01); *A61B 1/0646* (2013.01); *A61B 1/0676* (2013.01); *A61B 1/0684* (2013.01)

(58) Field of Classification Search
USPC ........... 600/27, 28, 29, 30, 31, 156, 104–108, 600/117, 118, 127, 129, 158, 159, 160, 169, 600/178–180; 607/100–104; 606/27–31, 606/15; 356/51; 359/350–361; 362/574
See application file for complete search history.

(56) References Cited

U.S. PATENT DOCUMENTS

| | | | |
|---|---|---|---|
| 4,402,311 A | 9/1983 | Hattori | |
| 4,409,993 A | 10/1983 | Furihata | |
| 4,872,458 A * | 10/1989 | Kanehira et al. ................. | 606/31 |
| 5,529,067 A * | 6/1996 | Larsen et al. ................. | 600/374 |
| 6,354,519 B1 | 3/2002 | Kidooka et al. | |
| 6,937,885 B1 | 8/2005 | Lewis et al. | |
| 2003/0040742 A1* | 2/2003 | Underwood et al. ........... | 606/32 |
| 2003/0065315 A1* | 4/2003 | Hareyama et al. .............. | 606/11 |
| 2003/0069485 A1 | 4/2003 | Konishi et al. | |
| 2003/0176768 A1* | 9/2003 | Gono et al. ................... | 600/109 |

(Continued)

FOREIGN PATENT DOCUMENTS

| | | |
|---|---|---|
| EP | 1 273 274 A1 | 1/2003 |
| FR | 2 849 963 | 7/2004 |

(Continued)

OTHER PUBLICATIONS

European extended Search Report dated Dec. 18, 2009.

*Primary Examiner* — Ryan Henderson
(74) *Attorney, Agent, or Firm* — Scully, Scott, Murphy & Presser, PC

(57) ABSTRACT

An endoscope includes an insert section to be inserted into the body cavity, an illumination window for directing illumination light therethrough and an observation window for observing an illuminated internal portion of the body cavity, arranged at a distal end portion of the insert section, and a blood flow changing section for changing a blood flow of blood flowing through a vessel in a near-surface region of a living organ inside the body cavity by providing one of a temperature change and vibration energy.

15 Claims, 22 Drawing Sheets

(56) References Cited

U.S. PATENT DOCUMENTS

| | | |
|---|---|---|
| 2004/0019120 A1 | 1/2004 | Vargas et al. |
| 2004/0102826 A1* | 5/2004 | Lasheras et al. ............ 607/105 |
| 2004/0266713 A1 | 12/2004 | Lu et al. |
| 2005/0096505 A1* | 5/2005 | Imaizumi et al. ............ 600/180 |
| 2005/0119527 A1* | 6/2005 | Banik et al. .................. 600/117 |
| 2005/0182321 A1 | 8/2005 | Frangioni |
| 2007/0051380 A1* | 3/2007 | Pasricha ....................... 128/898 |

FOREIGN PATENT DOCUMENTS

| | | | |
|---|---|---|---|
| JP | 5-103746 | 4/1993 | |
| JP | 5-103775 | 4/1993 | |
| JP | 2001-170009 | 6/2001 | |
| JP | 2001170009 A * | 6/2001 | ............ A61B 1/04 |
| JP | 2003-153911 | 5/2003 | |
| JP | 2003-290125 | 10/2003 | |
| JP | 2006-61621 | 3/2006 | |
| WO | WO 2005/099559 A1 | 10/2005 | |

* cited by examiner

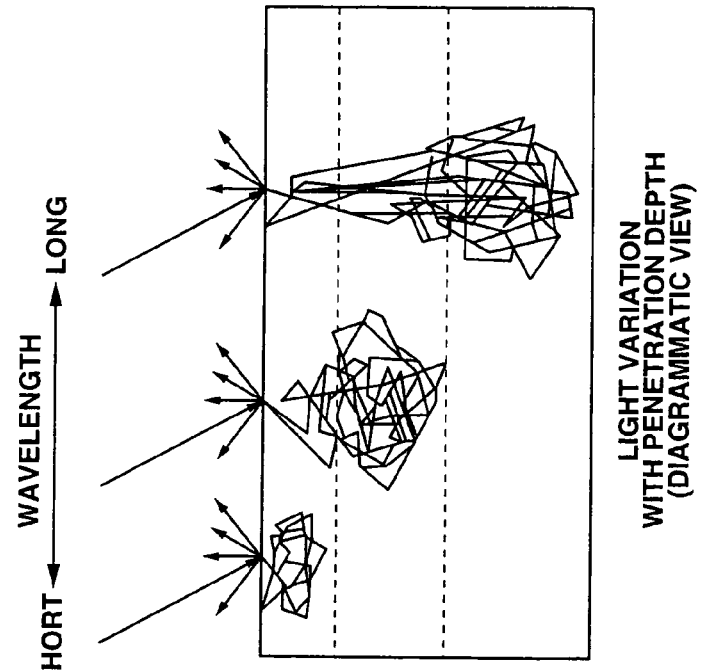
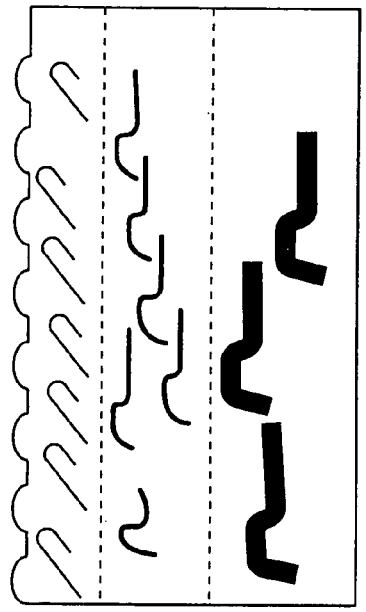
FIG.7A — CROSS-SECTIONAL STRUCTURE OF MUCOUS MEMBRANE (DIAGRAMMATIC VIEW)
FIG.7B — LIGHT VARIATION WITH PENETRATION DEPTH (DIAGRAMMATIC VIEW)

FAR INFRARED LIGHT
+ NBI LIGHT IRRADIATION

ENDOSCOPE, ENDOSCOPIC APPARATUS, AND EXAMINATION METHOD USING ENDOSCOPE

BACKGROUND OF THE INVENTION

1. Field of the Invention

The present invention relates to an endoscope to be inserted in a body cavity appropriate for observing vessels, an endoscopic apparatus, and an examination method of using the endoscope.

2. Description of the Related Art

Recently, endoscopes have been widely used in the medical field. Surgeons use the endoscopes to find and examine a lesion.

For example, cancers, as an example of lesion, tend to develop and cluster in vessels including a capillary vessel in a near-surface region of a living organ. Using an endoscope, a surgeon determines the presence or absence of a capillary vessel in the near-surface layer of the living organ and observes a network of the capillary vessel using the endoscope. The use of the endoscope in this way is becoming an effective method to determine whether a lesion is a cancer.

Thus, observing vessels containing capillary vessels in the near-surface layer of the living organ should be easy. However, the capillary vessel is too tiny to observe. More specifically, since the capillary vessel appears and disappears in synchronization with heart beat, it is difficult to observe it.

United States Patent Application Publication No. 2004/0266713 discloses means for promoting the supply of blood flow by using hypodermic injection.

United States Patent Application Publication No. 2004/0019120 discloses a method of administering a hyperosmotic agent for blood flow speed control.

SUMMARY OF THE INVENTION

An endoscope of one embodiment of the present invention includes an insert section to be inserted into the body cavity, an illumination window for directing illumination light therethrough and an observation window for observing an illuminated internal portion of the body cavity, arranged at a distal end portion of the insert section, and a blood flow changing section for changing a blood flow of blood flowing through a vessel in a near-surface region of a living organ inside the body cavity by providing one of a temperature change and vibration energy.

An endoscopic apparatus of another embodiment of the present invention includes an endoscope including an insert section to be inserted into the body cavity, an illumination window for directing illumination light therethrough and an observation window for observing an illuminated internal portion of the body cavity, arranged at a distal end portion of the insert section, and a blood flow changing section for changing a blood flow of blood flowing through a vessel in a near-surface region of a living organ inside the body cavity by providing one of a temperature change and vibration energy, and a light source for supplying the illumination light to the endoscope.

An examination method of one embodiment of the present invention includes a blood flow changing step for causing vessels including capillary vessels in the near-surface of a living organ in a body cavity to change blood flow by providing a temperature change to the surface of the living organ with a temperature changer, and an observation step of observing one of a vessel and blood flow changed in the blood flow changing step with the endoscope.

BRIEF DESCRIPTION OF THE DRAWINGS

FIGS. 7A and 7B diagrammatically illustrate the structure of a near-surface region of a mucous membrane and operation of an NBI observation mode.

DETAILED DESCRIPTION OF PREFERRED EMBODIMENTS

First Embodiment

Figure 1:
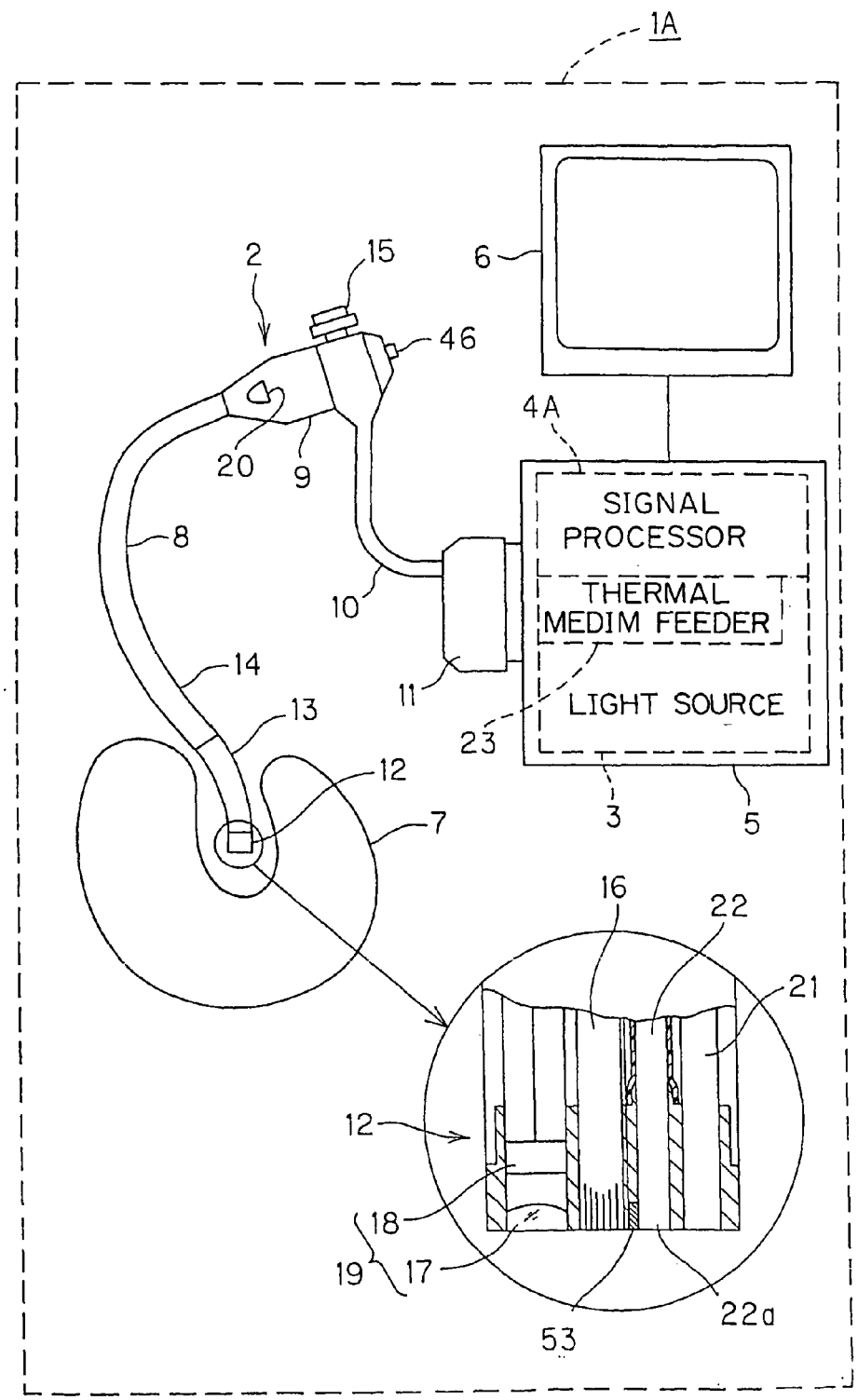
FIG. 1 illustrates the entire configuration of an endoscopic apparatus of a first embodiment of the present invention.
Figure 2:
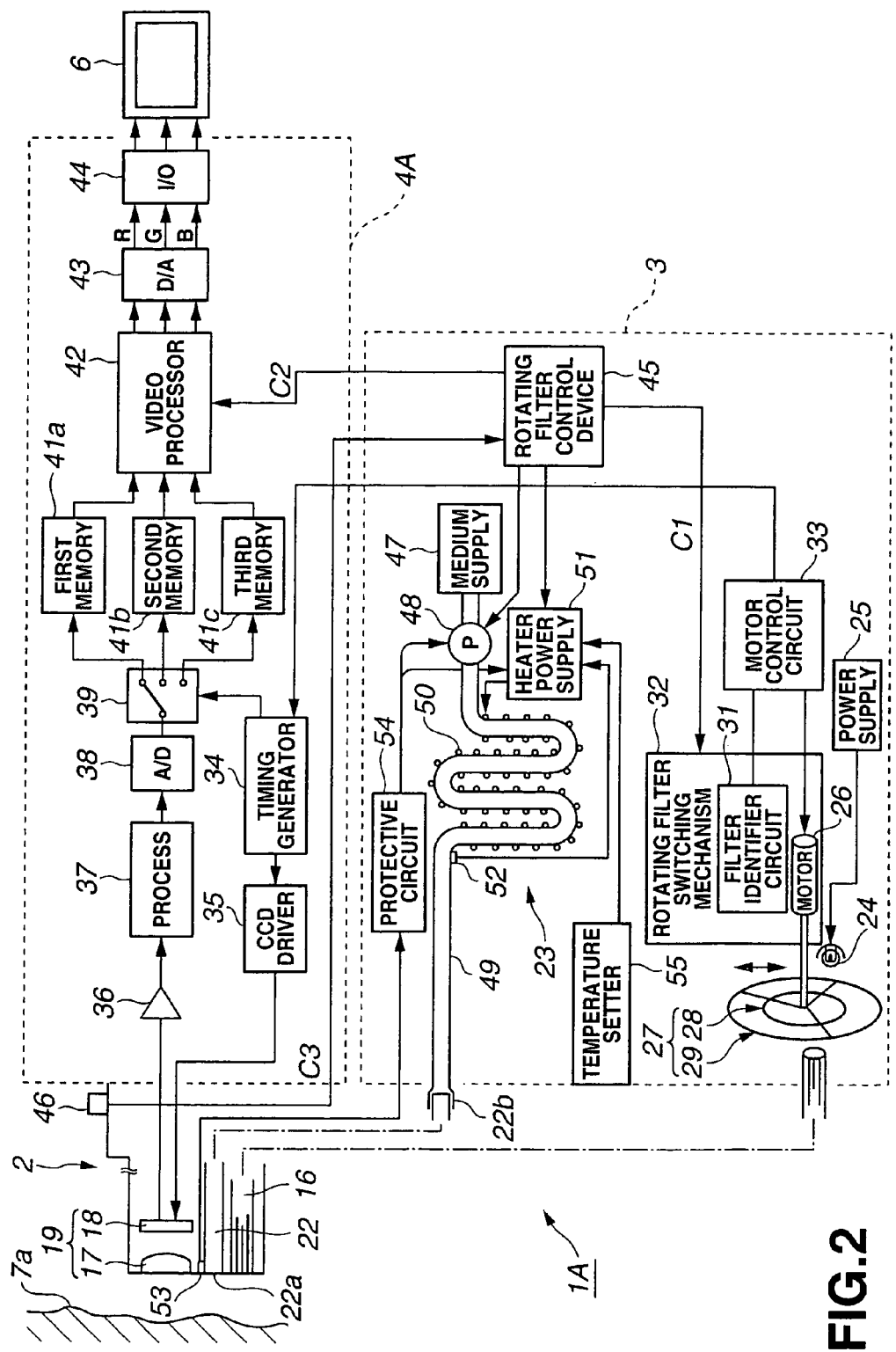
FIG. 2 is a block diagram illustrating in detail the endoscopic apparatus of FIG. 1.
Figure 3:
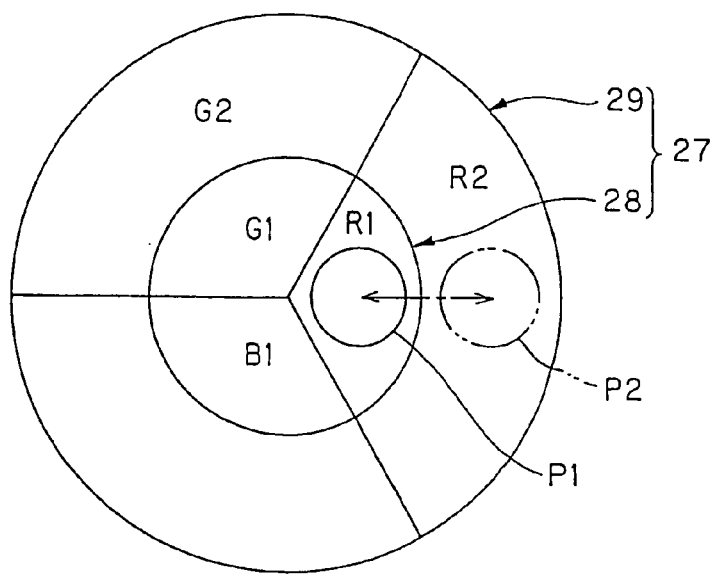
FIG. 3 illustrates the configuration of two filter sets provided to a rotating filter.
Figure 4:
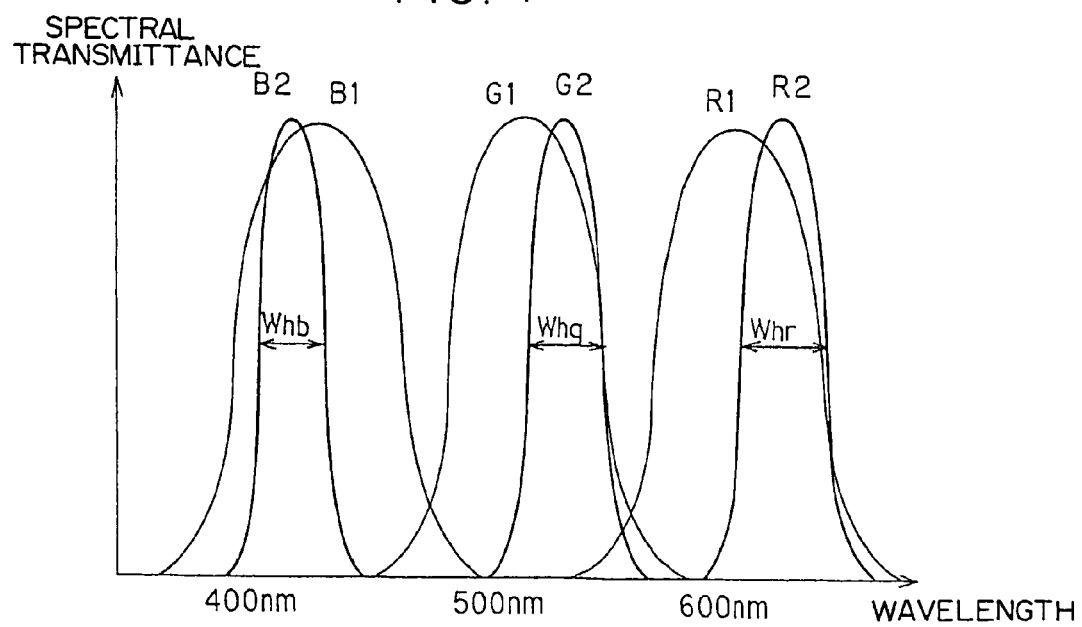
FIG. 4 illustrates spectral characteristics of each filter forming two filter sets of FIG. 3.
Figure 5:
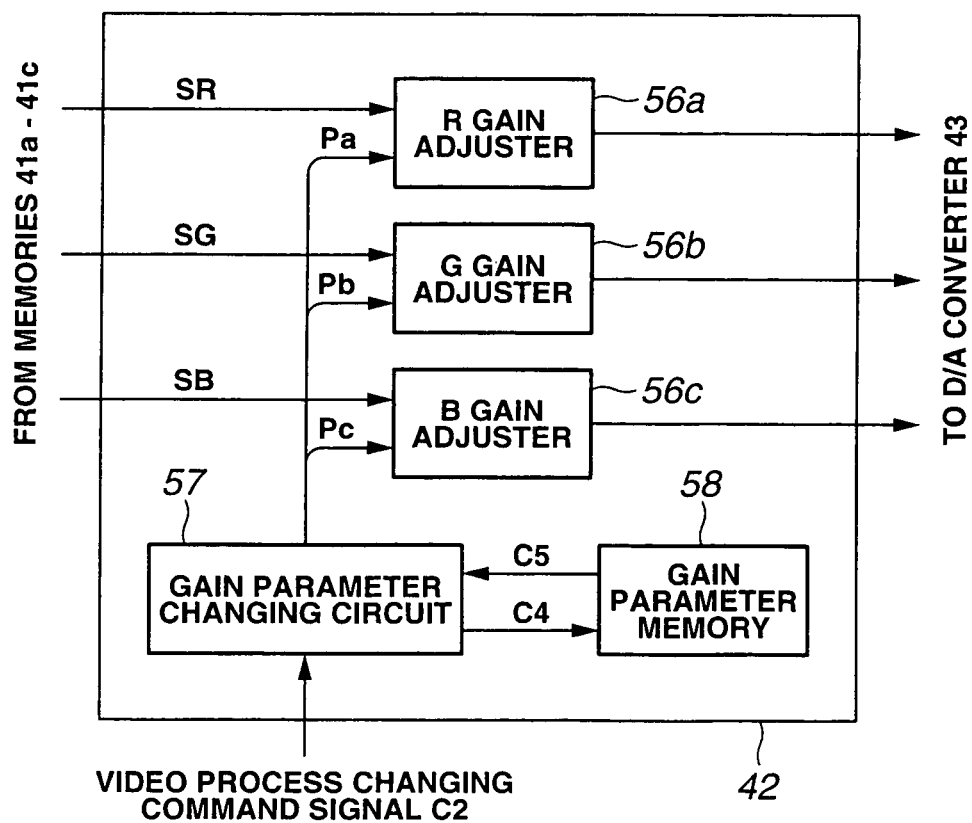
FIG. 5 is a block diagram illustrating a video processor.
Figure 6:
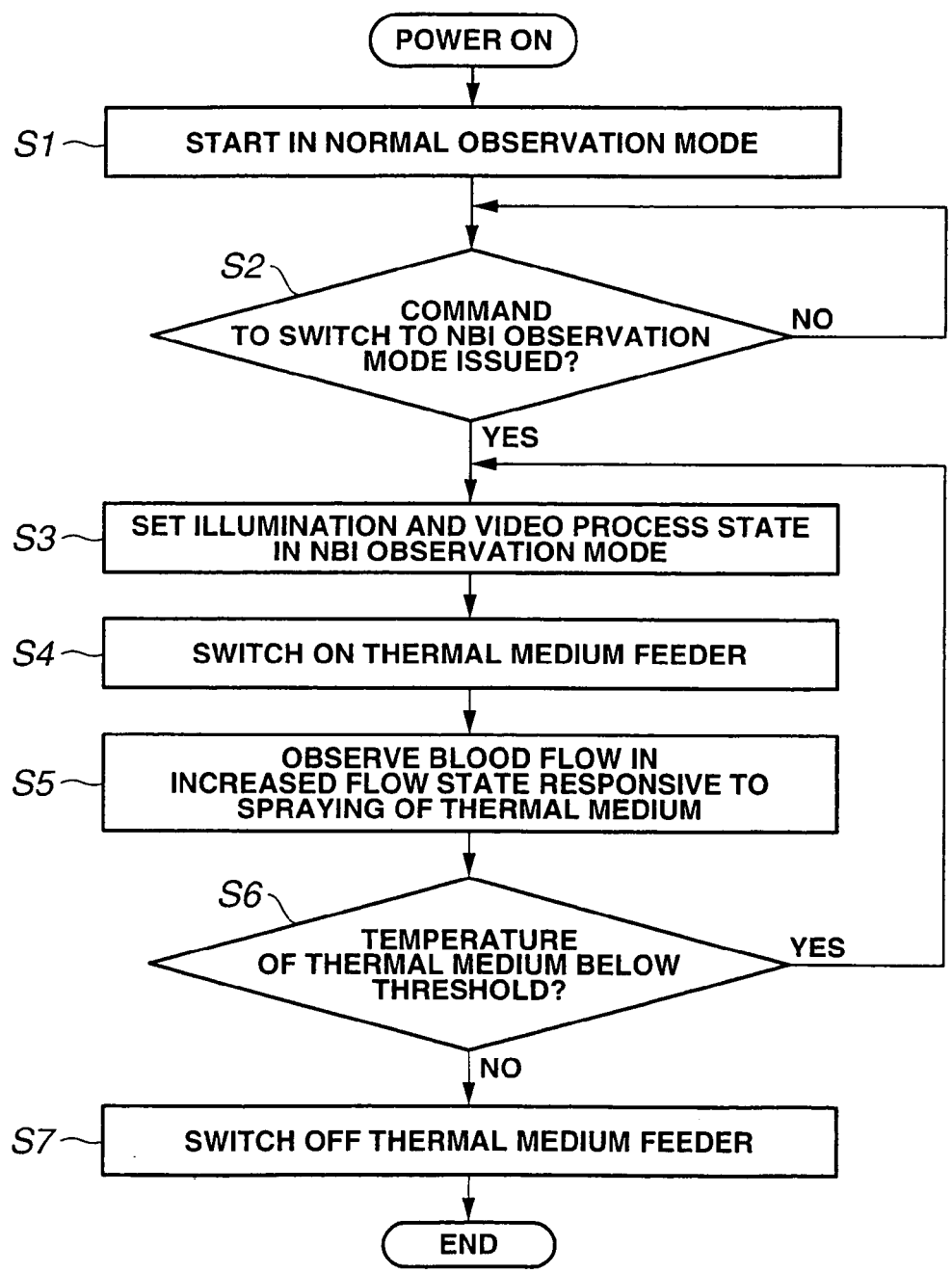
FIG. 6 is a flowchart illustrating operation of the present embodiment.

FIGS. 1 through 11 are related to a first embodiment of the present invention. FIG. 1 illustrates the entire configuration of an endoscopic apparatus of the present invention, FIG. 2 is a block diagram illustrating in detail the endoscopic apparatus of FIG. 1, FIG. 3 illustrates the configuration of two filter sets provided to a rotating filter, FIG. 4 illustrates spectral characteristics of each filter forming two filter sets of FIG. 3, FIG. 5 is a block diagram illustrating a video processor, and FIG. 6 illustrates operation of the present embodiment.

Figure 8:
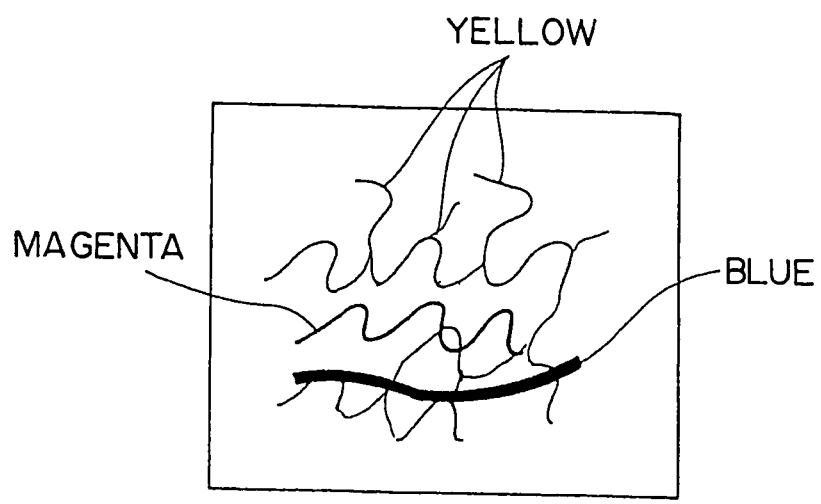
FIG. 8 diagrammatically illustrates a display example of a monitor screen which is shown when the mucous membrane is observed.
Figure 9:
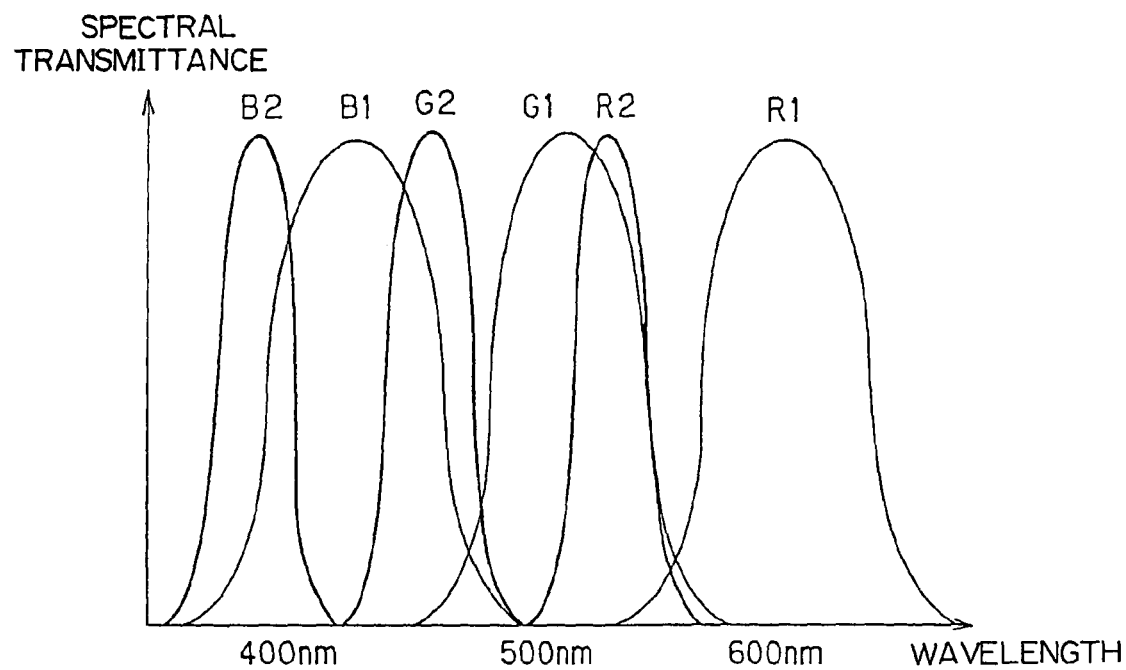
FIG. 9 illustrates transmission characteristics of a filter set of a first modification for use in the NBI observation mode.
Figure 10:
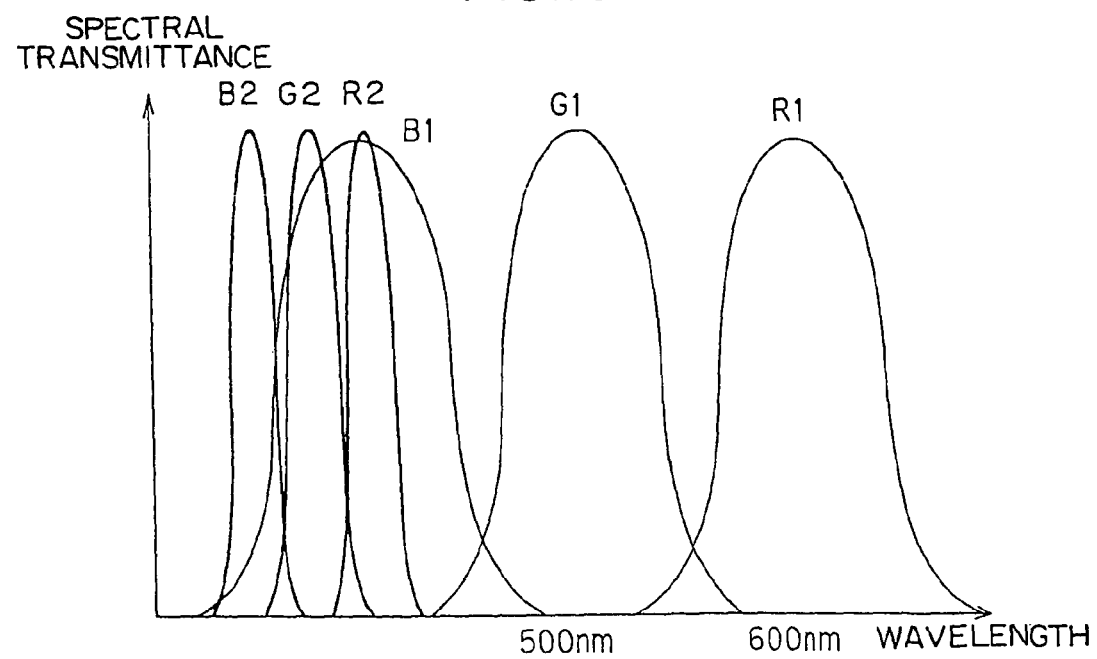
FIG. 10 illustrates transmission characteristics of the filter set of a second modification for use in the NBI observation mode.
Figure 11:
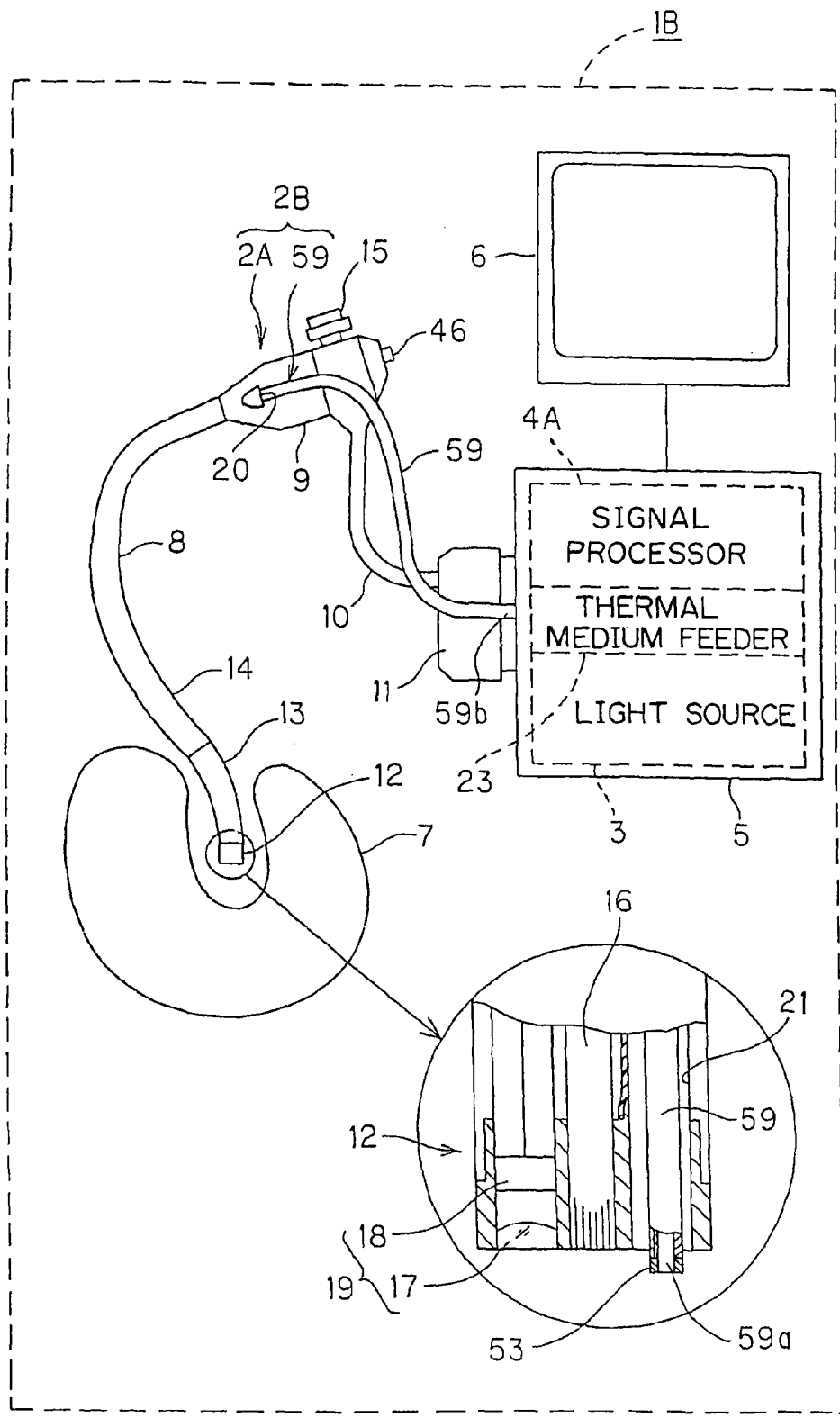
FIG. 11 illustrates the configuration of the endoscopic apparatus of a modification.

FIG. 7 diagrammatically illustrates operation of an NBI observation mode in the first embodiment, FIG. 8 diagrammatically illustrates a display example of a monitor screen which is shown when a mucous membrane is observed, FIG. 9 illustrates transmission characteristics of a filter set of a first modification for use in the NBI observation mode, FIG. 10 illustrates transmission characteristics of the filter set of a second modification for use in the NBI observation mode, and FIG. 11 illustrates the configuration of the endoscopic apparatus of a modification.

One object of the present embodiment is to provide an endoscope, an endoscopic apparatus, and an examination method of using the endoscope for distinctly observing the state and structure of a vessel and a blood flow through the vessel such as capillary vessel running in a near-surface area of a living organ in a body cavity. A further object of the present embodiment is to provide an endoscope, an endoscopic apparatus, and an examination method of using the endoscope for allowing users to observe the surface of the living organ in the body cavity, and a capillary vessel in the near-surface area of the living organ. The other embodiments have the same objects.

As shown in FIG. 1, an endoscopic apparatus 1A of the first embodiment of the present invention includes an electronic endoscope 2 having image pickup means, an observation apparatus 5 including a light source 3 for supplying illumination light to illumination light transmission means of the electronic endoscope 2, and a signal processor 4A for performing signal processing for the image pickup means, and an observation monitor 6 for displaying a video signal output from the observation apparatus 5.

The electronic endoscope 2 includes an elongated insert unit 8 to be inserted into a living organ 7 (in a body cavity) of a patient or the like, an operation unit 9 arranged at the proximal end of the insert unit 8, an universal cable 10 extended from the operation unit 9, and a connector 11 arranged at the proximal end of the universal cable 10. The connector 11 is detachably connected to the observation apparatus 5.

The insert unit 8 includes a distal end portion 12, a flexibly curvable portion 13 arranged at the proximal end of the distal end portion 12, and a flexible portion 14 extending to the distal end of the operation unit 9 from the proximal end of the curved portion 13. The operation unit 9 is provided with a curvature knob 15. Using the curvature knob 15, a user such as a surgeon can curve the curvable portion 13.

A light guide 16 is inserted through the insert unit 8 (as shown in enlargement of FIG. 1). With the connector 11 connected to the observation apparatus 5, illumination light is supplied to a light incident end from the light source 3 as shown in FIG. 2.

The illumination light transmitted by the light guide 16 is output in a forward direction from the light guide distal end face thereof fixed to an illumination window of the distal end portion 12, and then illuminates the side of a mucous membrane 7a as a portion of the living organ 7 to be observed.

An objective lens 17, secured to the observation window arranged next to the illumination window on the distal end portion 12, focuses an optical image of the mucous membrane 7a illuminated. A charge-coupled device (hereinafter CCD) 18 as a solid-state image pickup device is arranged at a focus position, and the CCD 18 photoelectrically converts the focused optical image into an electrical image. The objective lens 17 and the CCD 18 form an image pickup unit 19 as the image pickup means.

An image signal, obtained as a result of photoelectrical conversion of the CCD 18, is signal processed into a standard video signal (image signal) by the signal processor 4A in the observation apparatus 5 and is then output to the observation monitor 6.

A tool insertion port 20, arranged near the distal end of the operation unit 9, communicates with a channel 21. A tool, such as biopsy forceps may be inserted through the channel 21 from the tool insertion port 20 and then an end portion of the forceps is projected out of the channel 21 to perform biopsy.

The electronic endoscope 2 includes a tubular passage 22 that runs longitudinally through the insert unit 8 and sends a thermal medium to the distal end thereof. The thermal medium fed through the tubular passage 22 is sprayed from a distal end opening 22a of the tubular passage 22 toward the mucous membrane 7a.

The tubular passage 22 is routed through the insert unit 8, the operation unit 9, and the universal cable 10, and then reaches a pipe sleeve 22b (see FIG. 2) attached to the connector 11. With the connector 11 detachably engaged with the observation apparatus 5, the pipe sleeve 22b is connected to a thermal medium feeder 23 in the observation apparatus 5.

FIG. 2 illustrates the light source 3 for generating the illumination light, the signal processor 4A and the thermal medium feeder 23 all housed in the observation apparatus 5.

The light source 3 includes a light source unit 24 for generating observation light in a wide range covering a visible-light region, from ultraviolet light to near infrared light. The light source unit 24 may be a xenon lamp, a halogen lamp or the like.

The light source unit 24 is powered from a power supply 25 for light generation. Arranged in front of the light source unit 24 is a rotating filter 27 rotated by a motor 26 as shown in FIG. 3.

As shown in FIG. 3, the rotating filter 27 has a dual structure, namely, includes two sets of filters 28 and 29, one on an inner ring portion and the other on an outer ring portion.

The first filter set 28 on the inner ring portion includes three filters of R1, G1, and B1 for standard observation, and the second filter set 29 on the outer ring portion includes three filters R2, G2, and B3 for special observation purposes for vessel observation, more specifically for narrow-band imaging (hereinafter NBI). The first filter set 28 and the second filter set 29 are set for spectral transmittances for respective imaging purposes.

More specifically, filters 28a, 28b, and 28c for allowing light rays in wavelength regions of red (R1), green (G1), and blue (B1) for normal imaging to pass therethrough are circularly arranged, and outside these filters 28a, 28b, and 28c, filters 29a, 29b, and 29c for allowing light rays in wavelength regions of R2, G2, and B2 to pass therethrough are arranged.

FIG. 4 illustrates spectral transmission characteristics of each filter of the first filter set 28 and the second filter set 29 of FIG. 3 with wavelengths. The filters of R1, G1, and B1 forming the first filter set 28 of FIG. 4 typically have the same characteristics as R, G, and B filters widely used for light source devices for field sequential scanning.

In contrast, the R2, G2, and B2 filters forming the second filter set 29 are different in characteristic from the R, G, and B filters widely used for the light source device for field sequential scanning, and have narrow half-band width values Whr, Whg, and Whb. Although R2, G2, and B2 fall within the wavelength ranges of R, G, and B, respectively, the center frequencies of R2, G2, and B2 are deviated from the center frequencies of the R, G, and B light so that the resulting wavelengths of R2, G2, and B2 are appropriate for observing a vessel structure in the near-surface region of the mucous membrane 7a as described later.

That is, when the mucous membrane 7a is illuminated by the light rays having passed through the R2, G2, and B2 filters, transmission depth (penetration transmission) becomes different from one ray to another.

Thus, a captured image of the living mucous membrane 7a illuminated with the filtered light rays responds to the transmission depth of the light with the wavelength. By displaying the images with different colors, regions different in transmission depth are displayed in different colors.

The light source 3 includes a filter identifier circuit 31. The filter identifier circuit 31 identifies which one of the inner ring filter set and the outer ring filter set is arranged in an illumination optical path of the light source unit 24 of FIG. 2, thereby identifying the light ray illuminating a region to be observed.

The light source 3 also includes a rotating filter switching mechanism 32. The rotating filter switching mechanism 32 selectively sets the first filter set 28 on the inner ring portion and the second filter set 29 on the outer ring portion in the illumination optical axis that extends from the light source unit 24 to the light input end face of the light guide 16.

During the standard observation mode, the rotating filter switching mechanism 32 shifts the entire rotating filter 27 in the illumination light axis so that a light beam P1 (represented by solid line in FIG. 3) from the light source unit 24 is in alignment with the inner ring first filter set 28.

During the NBI observation mode, the rotating filter switching mechanism 32 shifts the entire rotating filter 27 in the illumination light axis so that a light beam P2 (represented by broken line in FIG. 3) from the light source unit 24 is in alignment with the outer-ring second filter set 29.

The rotating filter switching mechanism 32 is designed to shift the motor 26 and the filter identifier circuit 31 relative to the light source unit 24. Alternatively, the light source unit 24 may be shifted in an opposite direction.

The motor 26 rotates under the control of a motor control circuit 33.

Light rays of the wavelength regions Ri, Gi, and Bi (i=1 or 2) passed through the rotating filter 27 and separated time-sequentially are incident on the input end of the light guide 16, guided by the light guide 16 to the output end thereof, output in a forward direction from the output end thereof, and illuminates an area to be observed, such as the living mucous membrane 7a.

To identify the light beam illuminating the observation area, a filter identification signal F1 output from the filter identifier circuit 31 in the light source 3 is transferred to a timing generator 34 via the motor control circuit 33 that controls the motor 26. The timing generator 34 outputs to a CCD driver 35 and the like a timing signal synchronized with the filter identification signal F1.

A returning light beam reflected from the observation area such as the illuminated living mucous membrane 7a is focused on the CCD 18, and then photoelectrically converted by the CCD 18. The CCD 18 is supplied with a drive pulse from the CCD driver 35 in a signal processor 4A via a signal line, and reads an electrical signal (video signal) responsive to an image of the living mucous membrane 7a photoelectrically converted in response to the drive pulse.

The drive pulse is thus used to accumulate charge onto the CCD 18 during an open period of the rotating filter 27 (period throughout which an observation light beam illuminates the observation area) and reads the charge accumulated on the CCD 18 during a light blocking period (period throughout which the observation light beam does not illuminate the observation area).

FIG. 3 does not show a blocking area for simplicity. In practice, however, a blocking area is arranged between the R1 filter and the B1 filter. When the light beam is directed to the light blocking area, it becomes a light blocking period.

The charge read from the CCD 18 is supplied to a pre-amplifier 36 arranged in the electronic endoscope 2 or the observation apparatus 5 via a signal line as an electrical signal. A video signal amplified by the pre-amplifier 36 is supplied to a processor circuit 37 where signal processing including γ correction and white balance process and the like is performed. The resulting signal is then A/D converted into a digital signal by an A/D converter 38.

A selector circuit 39 causes three memories, namely, a first memory 41a, a second memory 41b, and a third memory 41c arranged corresponding to red (R), green (G), and blue (B) to selectively to store the digital video signal.

Color signals Ri, Gi, and Bi respectively stored on the first memory 41a, the second memory 41b, and the third memory 41c (represented by SR, SG, and SB in FIG. 5) are concurrently read, and input to a video processor 42. The video processor 42 performs video processing on the color signals.

An output signal from the video processor 42 is converted into analog color signals (represented by R, G, and B for simplicity in FIG. 2) by a D/A converter 43, and then output as R, G, and B color signals to the observation monitor 6 via an input-output interface (I/O) 44. The observation monitor 6 displays the observation area such as the living mucous membrane 7a and the like in color.

The endoscopic apparatus 1A further includes a rotating filter control device 45 in the light source 3. When a user operates an observation mode switch 46 for switching observation modes of the electronic endoscope 2, the rotating filter control device 45 outputs to the rotating filter switching mechanism 32 a rotating filter switch command signal C1 corresponding to the switching of observation mode.

At the moment the rotating filter 27 is switched, the rotating filter control device 45 issues a video process change command signal C2 to the video processor 42 to change video processing.

The signal processor 4A in the observation apparatus 5 includes the timing generator 34 for generating timings of the entire system. The timing generator 34 maintains the motor control circuit 33, the CCD driver 35, the selector circuit 39, etc. in synchronization.

The operation unit 9 in the electronic endoscope 2 includes an observation mode switch 46 including a scope switch for issuing a switch command of observation mode.

When the user operates the observation mode switch 46, a mode switch command signal C3 is transferred to the rotating filter control device 45. The rotating filter control device 45 then outputs the rotating filter switch command signal C1 or the like to switch from the standard observation mode to the NBI observation mode or from the NBI observation mode to the standard observation mode.

A thermal medium feeder 23 arranged in the light source 3 includes a pump 48 for conveying a medium such as air or water prior to heating from a medium supply 47, a pipe 49 serving as a passage for conveying the medium from the pump 48 to the pipe sleeve 22b, and a heater 50 serving as a heater unit wrapped around a part of an outer circumference of the pipe 49. The heater 50 performs a heating operation with power for heating supplied from a heater power supply 51.

The medium passing through the pipe 49 where the heater 50 is wrapped around is heated to a fixed temperature by the heater 50 and conveyed to a tubular passage 22 within the electronic endoscope 2 via the pipe sleeve 22b.

A temperature sensor 52 is arranged on the outer circumference of the pipe 49 close to the end of the heater 50 to detect the temperature of the medium heated by the heater 50. Information about the temperature detected by the temperature sensor 53 is input the heater power supply 51.

The heater power supply 51 controls heater power or the like so that the temperature detected by the temperature sensor 52 becomes a temperature set in a temperature setter 55 to be discussed later slightly higher than a temperature of the inside of a body cavity, namely, a normal temperature of the living mucous membrane 7a.

A temperature sensor 52 is also arranged in the vicinity of the distal end opening 22a of the tubular passage 22. Temperature information about a temperature detected by the temperature sensor 53 is input to a protective circuit 54. The protective circuit 54 determines whether a temperature detected by the temperature sensor 53 is equal to or lower than a threshold value. The threshold value is used to determine whether the temperature of the medium detected by the temperature sensor 53 is too high relative to the living mucous membrane 7a.

When the detected temperature of the thermal medium is above the threshold temperature value, the protective circuit 54 stops the feeding of the medium from the pump 48 while also stopping the operation of the heater power supply 51. The protective circuit 54 thus performs a protective operation to stop the spraying of the thermal medium above the threshold temperature value.

The user operates the temperature setter 55 connected to the heater power supply 51, and can thus variably set a temperature at which the heater 50 performs the heating operation. Taking into consideration a temperature drop caused while passing through the tubular passage 22 in the temperature of the thermal medium set as a result of heating by the heater 50, the user sets a temperature slightly higher than a temperature of the medium the user desires to spray from the distal end opening 22a.

The protective circuit 54 operates independent of the setting operation of the temperature setter 55, and performs the protective function thereof overriding the function of the temperature setter 55.

The rotating filter control device 45 controls the operation of the thermal medium feeder 23 in response to the switching from the standard observation mode to the NBI observation mode.

More specifically, in response to the switching from the standard observation mode to the NBI observation mode, the rotating filter control device 45 switches on the heater power supply 51 and switches on the pump 48. Conversely, in response to the switching from the NBI observation mode to the standard observation mode, the rotating filter control device 45 switches off the heater power supply 51 and switches off the pump 48.

FIG. 5 illustrates the specific configuration example of the video processor 42.

R, G, and G gain adjusters 56a, 56b, and 56c receive, from the memories 41a, 41b, and 41c, color signals SR, SG, and SB captured under illumination light rays Ri, Gi, and Ri (more specifically, color signals R, G, and B captured under the illumination light rays R1, G1, and B1 and color signals R, G, and B captured under the illumination light rays R2, G2, and B2). The R, G, and G gain adjusters 56a, 56b, and 56c gain adjust the color signals SR, SG, and SB at gains set by gain parameters Pa, Pb, and Pc from a gain parameter changing circuit 57, and then output gain adjusted signals to a D/A converter 43.

The gain parameter changing circuit 57 outputs, to the R, G, and G gain adjusters 56a, 56b, and 56c, gain parameters Pa, Pb, and Pc responsive to the video process change command signal C2 from the rotating filter control device 45.

In this case, the video processor 42 includes a gain parameter memory 58. In response to the inputting of the video process change command signal C2, the gain parameter changing circuit 57 applies to the gain parameter memory 58 a gain parameter read request command signal C4 for reading the gain parameters stored beforehand on the gain parameter memory 58.

The gain parameter changing circuit 57 causes the gain parameter memory 58 to output a corresponding gain parameter set C5, and supplies the R, G, and G gain adjusters 56a, 56b, and 56c with the gain parameters Pa, Pb, and Pc forming the gain parameter set.

The major functions of the present embodiment are discussed below. When the user issues a switch command to switch from the standard observation mode to the NBI observation mode, the thermal medium feeder 23 becomes initiated. Then, the thermal medium is then sprayed onto the observation area such as the living mucous membrane 7a or the like from the distal end opening 22a of the tubular passage 22 arranged in the electronic endoscope 2. A temperature change is provided to the surface of the observation area to a temperature state higher than a normal temperature state.

With the temperature shifting to a higher temperature, vessels in the near-surface region of the observation area expand, thereby increasing blood flow through the vessels, and thus allowing the vessels to be more easily observed. In accordance with the present embodiment, the electronic endoscope 2 has a function of blood flow changing means that provides a change to the vessels in the near-surface region of the observation area by spraying the thermal medium from the distal end opening 22a. In this case, since the capillary vessels run in the near-surface region of a living organ, the blood flow of the capillary vessels increases, thereby allowing the user to more easily observe the capillary vessels.

Operation of the present embodiment is described below with reference to a flowchart of an examination method of FIG. 6. The examination method includes as major steps a blood flow changing step by warming the living mucous membrane 7a during the NBI observation mode and an endoscopic observation step with the blood flow changed.

As shown in FIG. 1 or FIG. 2, a surgeon connects the electronic endoscope 2 to the observation apparatus 5 to perform endoscopy, and turns on an unshown power switch of the observation apparatus 5. With power on, the rotating filter control device 45 sets illumination and observation state (image processing) for the standard observation mode in step S1 of FIG. 6.

More specifically, the rotating filter control device 45 performs a control process to place the first filter set 28 in alignment with the illumination optical axis. In this condition, a white light ray from the light source unit 24 passes through the first filter set 28 having the same characteristics as those of the standard R, G, and B filters shown in FIG. 4. The light source 3 supplies frame-sequential illumination light rays of R1, G1, and B1 to the light guide 16, thereby illuminating the observation area such as the living mucous membrane 7a with the frame-sequential illumination light rays of R1, G1, and B1.

The observation area illuminated with the frame-sequential illumination light rays of R1, G1, and B1 is image-captured by the CCD 18 of the image pickup unit 19. The R, G, and B video signals (color signals) output from the CCD 18 are converted into digital signals by the signal processor 4A, and then successively stored onto the first memory 41a, the second memory 41b, and the third memory 41c.

The R, G, and B color signals temporarily stored on the first memory 41a, the second memory 41b, and the third memory 41c are also concurrently read, and input to the video processor 42. The video processor 42 performs image processing on the R, G, and B color signals.

The image processed color signals are converted into analog color signals by the D/A converter 43, and then displayed as a color image of the observation area of the living organ 7 on the observation monitor 6.

During the standard observation mode, the first filter set 28 covering the entire visible light range is used to reproduce a natural color. Subsequent to step S1 of FIG. 6, the rotating filter control device 45 monitors switching to the NBI observation mode in step S2.

The surgeon may switch to the NBI observation mode to observe more in detail the network of the vessels including the capillary vessels in the near-surface region of the observation area. To switch to the NBI observation mode, the surgeon operates the observation mode switch 46.

In response to the mode switch command signal C3 generated in response to the operation of the observation mode switch 46, the rotating filter control device 45 detects the switch command to the NBI observation mode.

In step S3, the rotating filter control device 45 performs a control process to shift the rotating filter 27 to set the illumination state of the NBI observation mode. In this case, the second filter set 29 in the rotating filter 27 is set to be in alignment with the illumination optical axis. The rotating filter control device 45 thus switches the video processing of the video processor 42 to the NBI observation mode.

Further to the above description, the rotating filter control device 45 outputs to the rotating filter switching mechanism 32 the rotating filter switch command signal C1. The rotating filter switching mechanism 32 shifts the rotating filter 27 upward in FIG. 2 (leftward in FIG. 3), thereby aligning the light beam P2 from the light source unit 24 to the second filter set 29. With this condition set, the filter identifier circuit 31 detects the condition, thereby ending a rotating filer switch operation.

During the NBI observation mode, the filters R2, G2, and B2 of FIG. 4 have narrower half-band width values Whr, Whg, and Whb in light transmission characteristics than R1, G1, and B1, and luminance levels of resulting signals drop.

Consequently, in response to the switching to the second filter set 29, the rotating filter control device 45 outputs the video process change command signal C2 to the video processor 42. The rotating filter control device 45 performs the control process to result in an image appropriate for examination, for example, by increasing the gains of the R, G, and G gain adjusters 56a, 56b, and 56c to be higher than those for the standard observation mode.

During the NBI observation mode in the present embodiment, gain setting is performed so that an image (component image) obtained under the illumination through the R2, G2, and G2 filters reaches a luminance level easy to discriminate when displayed in different colors (easy to discriminate taking into consideration the recognition function of humans to color).

In accordance with the present embodiment, the rotating filter control device 45 turns on the operation of the thermal medium feeder 23 in step S4 in response to the setting in step S3. The thermal medium generated by the thermal medium feeder 23 flows through the tubular passage 22 of the electronic endoscope 2 and is then sprayed to the observation area from the distal end opening 22a.

Through the spraying of the thermal medium in step S5, the temperature of the vessels in the observation area rises and the vessels expand thereby causing the blood flow change to increase blood flow. The surgeon observes (examines) the vessels such as the capillary vessels and the blood flow with the electronic endoscope 2 with the blood flow increased (changed).

The protective circuit 54 monitors in step S6 whether the temperature of the thermal medium detected by the temperature sensor 53 is equal to or lower than the threshold value. If it is determined that the detected temperature is equal to or lower than the threshold value, processing returns to step S3 to observe the vessels with the blood flow increased during the NBI observation mode.

Meanwhile, if the detected temperature is above the threshold value, the protective circuit 54 immediately turns off the operation of the thermal medium feeder 23. With the feeding operation of the pump 48 stopped, the spraying operation of the thermal medium from the distal end opening 22a immediately stops. Also, the supplying of the heater power from the heater power supply 51 to the heater 50 is cut off, and the heater 50 stops heating. The protective operation is thus performed.

The NBI observation mode is appropriate for observing the cross-sectional structure of the mucous membrane as shown in FIG. 7A.

The near-surface region of the living mucous membrane 7a, such as a mucous membrane of the stomach, is now observed as the observation area.

The typical cross section of the near-surface region of the mucous membrane is shown as in FIG. 7A. The mucous membrane includes a surface irregular structure, a capillary network at a near-surface layer, vessels larger than the capillary vessels at a layer slightly deeper, and a large-vessel network at a deeper layer.

When the living mucous membrane is observed, the observed image preferably shows the structure of vessels in detail. By observing the structure of the capillary vessel at the near-surface layer, early detection of a lesion such as a cancer becomes easy.

The light is used to observe the living mucous membrane in which vessels runs at the sub-layer. How the light penetrates the sub-surface layer depending on the wavelength thereof is shown in FIG. 7B. The shorter the wavelength of the visible light (blue light), the shallower the light penetrates the living organ. The longer the wavelength of the light (from green to red), the deeper the light penetrates the mucous membrane of the living organ.

The filter elements R1, G1, and B1 of the first filter set 28 for use in the standard observation mode have broad bands with wide half-band widths to cover the visible light region to achieve natural color reproduction as shown in FIG. 4. In these characteristics, light through the filter B1 as a short wavelength light contains light components in a wide wavelength range, and permit concurrent observation with a light ray having a shallow penetration depth and a light ray having an intermediate penetration depth.

As a result, a B image thus contains a mixture of signals from the capillary vessels at the near-surface layer to the vessels at the intermediate layer.

In contrast, the filter B2 of the second filter set 29 having a narrow-band width Whb limits the wavelength range of the light rays, and as a result, in comparison with the light ray B1 having broad characteristics, the ratio of light rays having a shallow penetration depth in the living mucous membrane becomes large. The image resulting from the B2 light rays increases contrast of the capillary network on the surface, and permits the near-surface structure to be observed easily.

From the graph plotting the spectral characteristics of the R1, G1, and B1 filters of the first filter set 28 and the R2, G2, and B2 filters of the second filter set 29 of FIG. 4, the filters for the NBI observation mode have narrow half-band values Whr, Whg, and Whb, and the center wavelengths are adjusted so that the bands are separated with no portion thereof overlapping each other.

The band width or half-band width value Whg of the G2 is set to be narrower than the filter G1, and the band of the G2 is separated from the band of the filter B2 along the wavelength axis. In the same way as in the B2 light rays, the half-band width Whg of the wavelength of the filter G2 is set to be narrow. The difference of the image from the filter B2 becomes distinct. The image from the filter G2 does not reflect the surface structure and the capillary vessels, while distinctly showing the vessel structure at the intermediate layer.

The band width or half bandwidth Whr of the filter R2 is set to be narrower than the filter R1. The band of the filter R2 is separated from the filter G2 along the wavelength axis. In this way, the image through the R2 filter reflects large vessels at the deeper layer alone.

The captured images through the bands of the filters R2, G2, and B2 are signal processed in a way similar to the standard observation mode except the gain adjustment through the video processor 42. The resulting image is displayed in color as RGB color signals on the observation monitor 6.

In this case, information about the vessel structure in depth direction is represented with color difference and resulting color differences are synthesized in color display. Unlike the standard observation mode, the vessel structure information is reproduced clearly.

More specifically, the capillary network at the near-surface layer is displayed yellow (G and R colors appearing with only B color absorbed), the vessel network at the intermediate layer is displayed magenta to red, and the large vessel at the deep layer is displayed blue-tinged.

Therefore, the vessel structure running at different depths as illustrated in FIG. 8 are diagrammatically shown different in color on the monitor screen of the observation monitor 6. The network of the vessels at different depths are clearly identified from the image.

The signals output to R, G, and B channels of the observation monitor 6 are switchably or selectively set so that the network of the capillary vessels may be displayed at a color tone preferred by the user.

Also, when the apparatus is switched to the NBI observation mode in the present embodiment as described above, a heated medium such as heated (warmed) air or water is sprayed onto the surface of the living mucous membrane 7a. The near-surface capillary vessels expand and are observed more easily by the user than when the heated medium is not sprayed.

In accordance with the present embodiment, an endoscopic image appropriate for standard observation is thus obtained. With the filter set switched, the network of the vessels at different depths in the near-surface layer of the living mucous membrane 7a can thus observed.

Since in particular, a large temperature change is provided to the capillary vessels running at the near-surface layer, the network of the vessels is more easily observed. The surgeon can smoothly examine the inside of the body cavity with the electronic endoscope 2.

As a first modification of the second filter set 29, the filter set may have characteristics of FIG. 9. In the first modification, the filter G2 in the second filter set 29 of FIG. 4 is arranged as a filter R2, and a filter G2 and a filter B2 having narrow half-bandwidths are shifted to a shorter wavelength side than the filter R2.

The filter G2 is slightly shifted to a shorter wavelength side than the filter G2 of FIG. 4 and the filter B2 is slightly shifted to a shorter wavelength side than the filter B2 of FIG. 4.

The second filter set 29 as the first modification is appropriate for observing in detail the surface roughness structure to the vessel network at the intermediate depth layer in different colors.

A filter set having characteristics of FIG. 10 may be used as a second modification of the second filter set 29. In the second modification, all filters R2, G2, and B2 are arranged in a short wavelength range so that scattering and absorption of light rays at the near-surface layer of the living mucous membrane are detected at high gain. These characteristics are appropriate for detecting early stage cancer developed at the near-surface layer of the living mucous membrane 7a.

Figure 23:
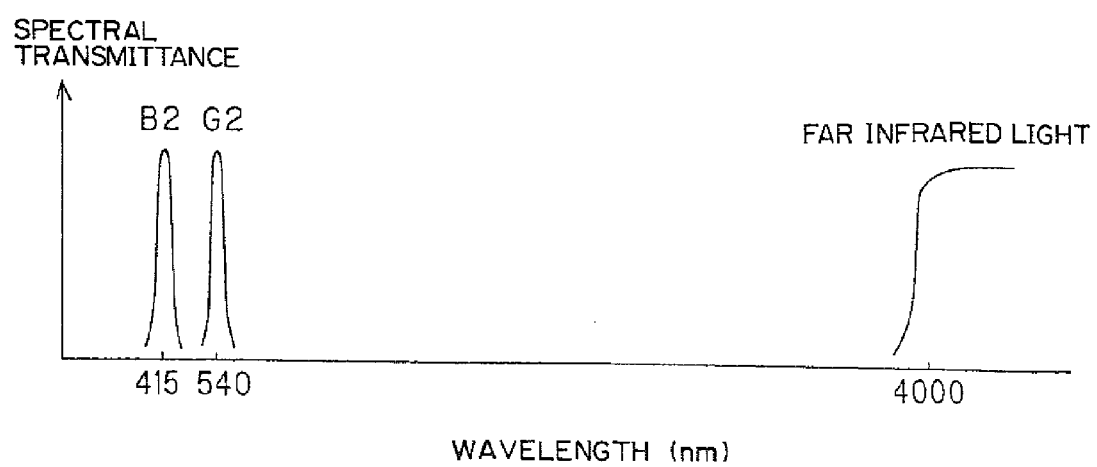
FIG. 23 diagrammatically illustrates spectral characteristics of a filter of FIG. 22.

During the NBI observation mode, the light source 3 may supply two narrow-band illumination light rays to the light guide 16. For example, as shown in FIG. 23, the light source 3 may supply two narrow-band illumination light rays G2 and B2 during the NBI observation mode.

In this case, the signal processor 4A may output two color signals corresponding to the illumination light rays to the observation monitor 6 to display the image in two colors. Furthermore, the signal processor 4A may output one of the two color signals to the two channels of the observation monitor 6 (in this case, an endoscopic image is displayed in three colors).

In the above description, the tubular passage 22 for spraying the thermal medium to the observation area is arranged within the electronic endoscope 2. A structure such as an endoscopic apparatus 1B of FIG. 11 may also be acceptable.

The endoscopic apparatus 1B employs an electronic endoscope 2B that includes a thermal medium spray tube 59 detachably loaded to the tool insertion port 20 in the electronic endoscope 2A.

FIG. 11 illustrates an electronic endoscopic portion 2A that permits the thermal medium spray tube 59 to be detachably loaded into a channel 21.

In the configuration as shown in FIG. 11, a sleeve 59b at the proximal end of the thermal medium spray tube 59 is detachably engaged with an end of a connection portion of the pipe 49 of the thermal medium feeder 23. The temperature sensor 53 is also arranged on the distal end opening of the thermal medium spray tube 59.

When the sleeve 59b is connected to the end of the pipe 49 (see FIG. 2), a detected signal of the temperature sensor 53 is supplied to the protective circuit 54 via an unshown electrical connection. The rest of the structure of the endoscopic apparatus 1B is identical to the endoscopic apparatus 1 of FIGS. 1 and 2. In this case, the electronic endoscope 2B has substantially the same functions as the electronic endoscope 2.

In the configuration of FIG. 11, the electronic endoscope 2B is embodied by loading the thermal medium spray tube 59 to an existing electronic endoscope 2A. For this reason, this modification advantageously increases applications.

As shown in FIG. 11, the end portion of the thermal medium spray tube 59 is projected out of the end opening of the channel 21. Alternatively, the end portion of the thermal medium spray tube 59 is placed within the tool insertion port 20 and the channel 21 is used as a passage of the thermal medium. In this case, the end opening of the channel 21 serves as a sprayer of the thermal medium.

In the first embodiment, the temperature sensor 53 is arranged to detect the temperature of the thermal medium when the heated (warmed) medium is sprayed. As in a sixth embodiment to be discussed later, a temperature sensor 94 for detecting the temperature of the living mucous membrane 7a in a non-contact fashion may be arranged.

Second Embodiment

Figure 12:
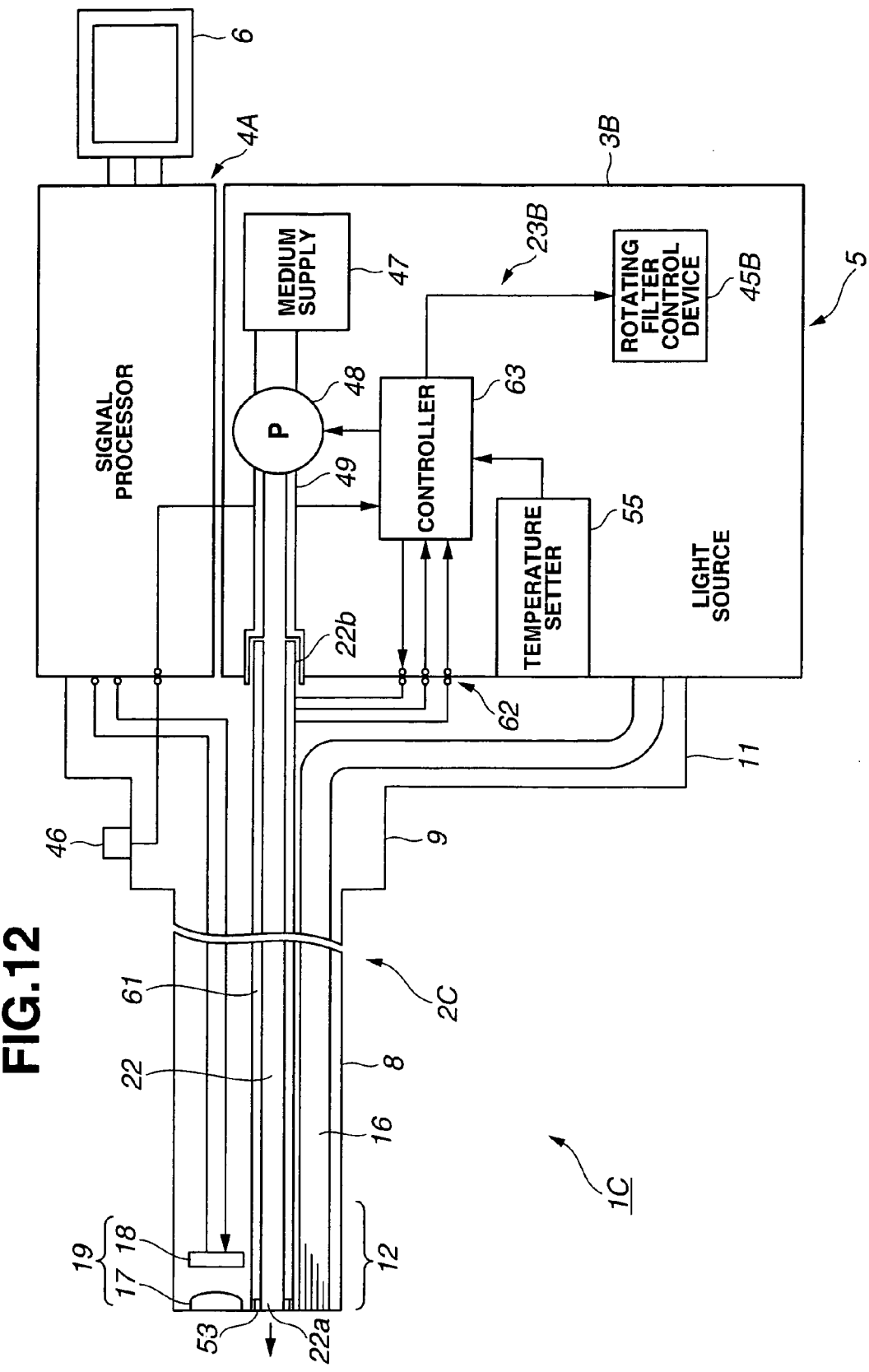
FIG. 12 is a configuration diagram illustrating an endoscopic apparatus in accordance with a second embodiment of the present invention.

Referring to FIG. 12, a second embodiment of the present invention is described below. FIG. 12 diagrammatically illustrates the configuration of an endoscopic apparatus 1C in accordance with the second embodiment of the present invention.

In accordance with the first embodiment, the thermal medium feeder 23 is arranged in the light source 3, and the thermal medium from the thermal medium feeder 23 is passed through the tubular passage 22 in the electronic endoscope 2 and then sprayed to the observation area. In contrast, the endoscopic apparatus 1C includes in a light source 3B a thermal medium feeder 23B, the medium of which is not yet heated, and a heater in the tubular passage 22 in an electronic endoscope 2C. The heated medium is sprayed from the distal end opening 22a of the tubular passage 22.

The thermal medium feeder 23B of FIG. 12 does not include the heater 50 and the heater power supply 51 of FIG. 2.

Meanwhile, the tubular passage 22 in the electronic endoscope 2C includes a heater and temperature sensor unit 61 into which a heater and a temperature sensor are integrated as a unitary body. Although the heater and the temperature sensor are integrated into a unitary body herein, the heater and the temperature sensor may be arranged as separate units.

When the connector 11 is connected to the observation apparatus 5, the heater and temperature sensor unit 61 is connected to a controller 63 in the thermal medium feeder 23B via electrical junctions 62.

In response to the inputting of the mode switch command signal C3 from the observation mode switch 46, the controller 63 controls the heater and temperature sensor unit 61 and the pump 48 in medium feeding. The controller 63 is also connected to the rotating filter control device 45B.

In accordance with the first embodiment, the rotating filter control device 45 also controls the thermal medium feeder 23. In the second embodiment, the controller 63 controls medium feeding and medium heating while the rotating filter control device 45B controls switching of the rotating filter 27 in response to the control process of the controller 63. The rest of the structure of the second embodiment is identical to the first embodiment.

Unless otherwise particularly noted, the operation in the standard observation mode in the second and subsequent embodiments remains unchanged from that in the first embodiment.

The operation of the second embodiment is similar to the operation of the first embodiment. In accordance with the second embodiment, the light source 3B connected to the electronic endoscope 2C is reduced in size. Since the heater is arranged in the electronic endoscope 2C in accordance with the second embodiment, the temperature drop of the thermal medium occurring in the way to the distal end opening 22a is reduced.

The remaining advantages of the second embodiment are substantially identical to those of the first embodiment.

In a modification of the second embodiment, the heater may be fabricated of a spiral member arranged in the insert unit 8, and the thermal medium flowing through the tubular passage 22 in the spiral member is thus heated.

In accordance with the second embodiment, the heater and temperature sensor unit 61 in the tubular passage 22 is integrally arranged with the electronic endoscope 2C in a unitary body. Alternatively, the modification of the first embodiment (structure described with reference to FIG. 11) may be applied. More specifically, a tube housing the heater and temperature sensor unit 61 is detachably inserted in the channel 21 of the electronic endoscope 2A of FIG. 11.

Third Embodiment

Figure 13:
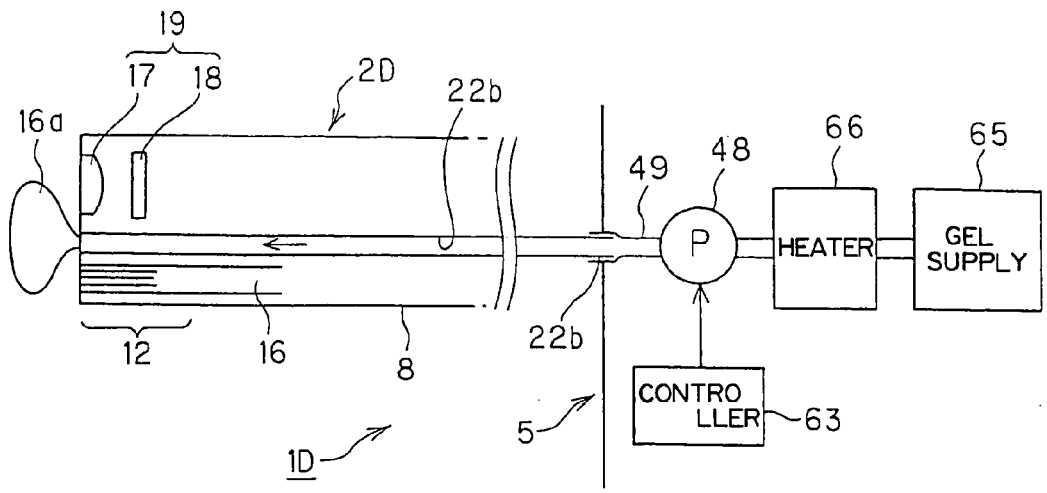
FIG. 13 is a configuration diagram illustrating a major portion of an endoscopic apparatus in accordance with a third embodiment of the present invention.

A third embodiment of the present invention is described below with reference to FIG. 13. FIG. 13 diagrammatically illustrates the configuration of a major portion of an endoscopic apparatus 1D of the third embodiment of the present invention. In accordance with the third embodiment, a medium, such as a thickener, changing viscosity thereof with temperature is used.

An electronic endoscope 2D sprays, from the distal end thereof, a medium in a liquid state to the observation area such as the living mucous membrane 7a. The sprayed medium has the function of raising the surface and near-surface region of the observation area in temperature, thereby increasing the blood flow. In addition to this function, the medium shifts to a large viscosity state when the medium drops in temperature, and tends to stay on the observation area. The medium thus has the function of covering the surface of the observation area and maintaining temperature (temperature insulation).

The endoscopic apparatus 1D of the third embodiment includes a gel supply 65 instead of the medium supply 47 in the endoscopic apparatus 1A of FIG. 2. The gel supply 65 stores a transparent thickener (or a solvent dissolving the thickener). The thickener becomes low in viscosity and fluid in a high temperature condition while becoming high in viscosity and gelated in a low temperature condition.

The gel supply 65 is connected to a heater 66 composed of a heater and a heater power supply. The heater 66 stores a thickener 66a that is almost in a fluid state as a result of being heated to a temperature slightly higher than the temperature of the living organ 7.

When the pump 48 is operated, the fluid thickener 66a heated by the heater 66 is fed to the tubular passage 22C in the electronic endoscope 2D via the pipe 49. The electronic endoscope 2D employs the tubular passage 22C instead of the tubular passage 22 in the electronic endoscope 2 of the first embodiment. The tubular passage 22C serves as a thickener passage that conveys the fluid thickener 66a to the end thereof, and the distal end opening 22a sprays the fluid thickener 66a.

In the third embodiment, the heater 66 is always in an operational state, and when switched to the NBI observation mode, the controller 63 sets the pump 48 from off to on. When switched to the standard observation mode, the pump 48 is turned off.

With the pump 48 turned on, the fluid thickener 66a is sprayed from the distal end opening 22a of the tubular passage 22.

The thickener 66a, when sprayed onto the living mucous membrane 7a, raises the surface layer of the living mucous membrane 7a in temperature as previously described in connection with the first embodiment, and expands the capillary vessels and the like for easy observation.

The rest of the configuration of the third embodiment remains unchanged from the above-described embodiments.

Operation of the third embodiment in response to the switching to the NBI observation mode is described below with reference to FIGS. 14A through 14C.

With the operation mode switched to the NBI observation mode, the controller 63 activates the pump 48.

Figure 14A:
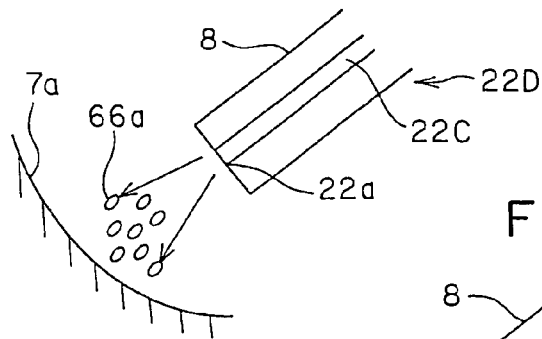
FIGS. 14A through 14C illustrate operation of the third embodiment.

The fluid thickener 66a heated by the heater 66 passes through the pipe 49 and the tubular passage 22C of the electronic endoscope 2A and is then sprayed from the distal end opening 22a as described in FIG. 14A.

More specifically, the fluid thickener 66a is sprayed from the distal end opening 22a onto the living mucous membrane 7a as the observation area.

The thickener 66a sprayed on the living mucous membrane 7a raises the surface layer of the living mucous membrane 7a in temperature and expands the capillary vessels for easy observation as previously described in connection with the first embodiment.

In this case, the thickener 66a then drops in temperature, and becomes high in viscosity. As shown in FIG. 14B, the thickener 66a becomes gelated into a thickener 66b with viscosity increased from the fluid state thereof. The thickener 66b tends to stay on the surface of the living mucous membrane 7a.

Moreover, the thickener 66b covers the surface of the living mucous membrane 7a, thereby maintaining the inner area at a high temperature.

Figure 14B:
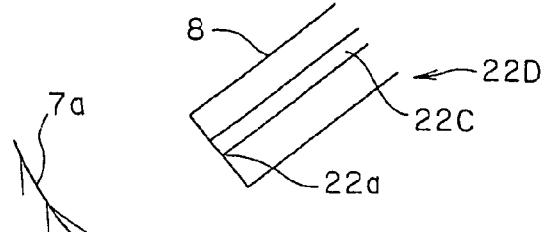
Figure 14C:
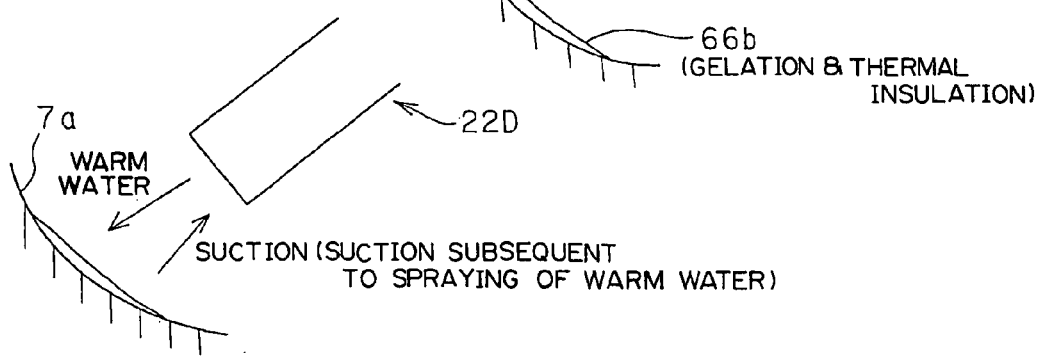

As shown in FIG. 14B, the gelated thickener 66b tends to stay on the mucous membrane and keep temperature. With the temperature maintenance property of the thickener 66b, the amount of sprayed medium is reduced, and the state in which the capillary network is observed in detail is thus maintained.

After observing the living mucous membrane 7a, the thickener 66b, if having biocompatibility, can be left there.

If a removable operation to remove the thickener 66b is performed, a warm water is sprayed onto the thickener 66b through an unshown pipe to restore the fluid thickener 66a. A distal end opening of the channel 21 having the function of a suction pipe suctions the fluid thickener 66a and discharges the suctioned thickener 66a to outside the body cavity.

In the above description, the pump 48 liquefies the thickener 66a and conveys the fluid thickener 66a through tubular passage 22C and sprays the thickener 66a from the distal end opening 22a.

In this case, depending on type, the thickener 66a may have no large viscosity even in its gelated state. In such a case, the thickener 66a is heated in the gelated state thereof to a temperature slightly higher than the temperature of the living mucous membrane 7a. Such thickener 66a is sprayed from the distal end opening 22a using pressure of the pump 48.

Fourth Embodiment

Figure 15:
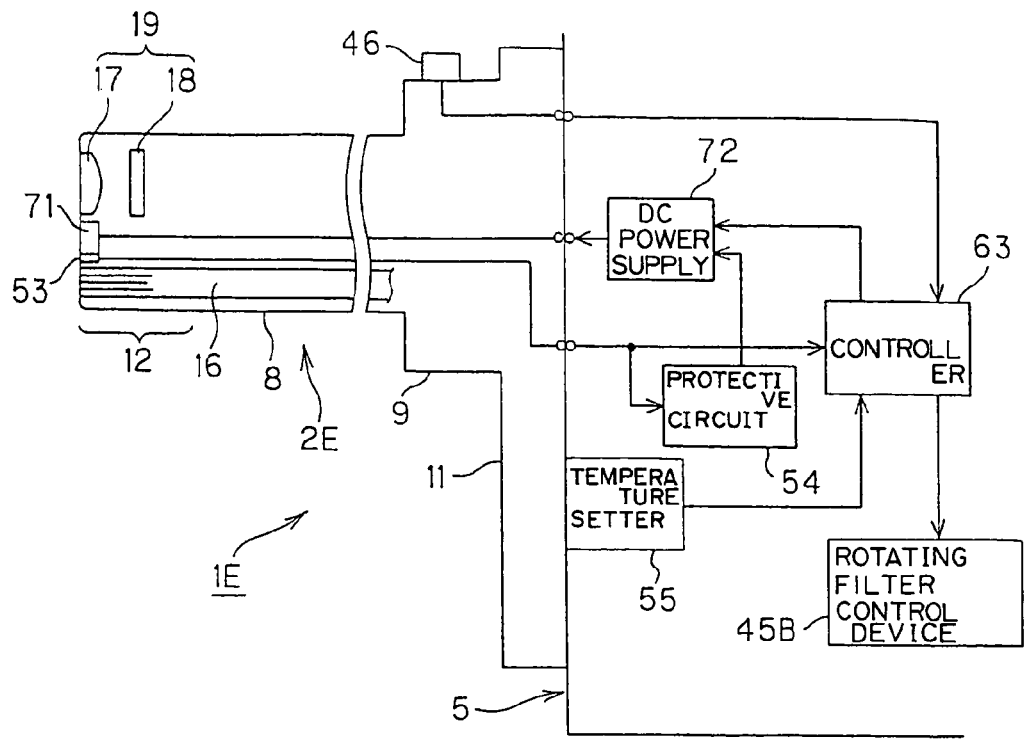
FIG. 15 is a configuration diagram illustrating a major portion of an endoscopic apparatus in accordance with a fourth embodiment of the present invention.

A fourth embodiment of the present invention is described below with reference to FIG. 15. FIG. 15 diagrammatically illustrates the configuration of a major portion of an endoscopic apparatus 1E in accordance with the fourth embodiment. In the fourth embodiment, a temperature control device (or heater device) is arranged at the end of a distal end portion 12 of the endoscopic apparatus 1E. The temperature control device provides a temperature change to the living mucous membrane 7a with the temperature control device in contact with the living mucous membrane 7a. A blood flow changes in the area of contact, and vessels there are easy to observe.

An electronic endoscope 2E of the fourth embodiment is without the tubular passage 22 for allowing the thermal medium to pass therethrough in the electronic endoscope 2 of the first embodiment (for example, the electronic endoscope 2A of FIG. 11). In the electronic endoscope 2E, a Peltier device 71 is arranged at the end face of the distal end portion 12 as a heater device for temperature control.

The temperature sensor 53 is arranged next to the Peltier device 71 to detect the temperature of the Peltier device 71.

The Peltier device 71 is connected to a DC power supply 72 arranged in the observation apparatus 5 via a power source line. When the NBI observation mode is set under the control of the controller 63, the DC power supply 72 supplies DC power to the Peltier device 71.

The controller 63 controls supplying of the DC power to the Peltier device 71 so that the Peltier device 71 reaches a temperature set by the user on the temperature setter 55. The temperature detected by the temperature sensor 53 is input to the controller 63 to be used for temperature control while also being input to the protective circuit 54. When the detected temperature rises above a threshold value, the protective circuit 54 turns off the DC power supply 72 so that no DC power is supplied to the Peltier device 71. The controller 63 is connected to the rotating filter control device 45B.

Since the fourth embodiment does not use the thermal medium described in connection with the first embodiment, no thermal medium feeder means is required in the observation apparatus 5.

Operation of the fourth embodiment is described below.

When a surgeon switches to the NBI observation mode, the controller 63 activates the DC power supply 72 while sending a signal to the rotating filter control device 45B for illumination for the NBI observation mode. The DC power supply 72 supplies DC power to the Peltier device 71. The DC power supply 72 under the control of the controller 63 controls DC power so that the temperature of the Peltier device 71 becomes the temperature set by the temperature setter 55.

Figure 16A:
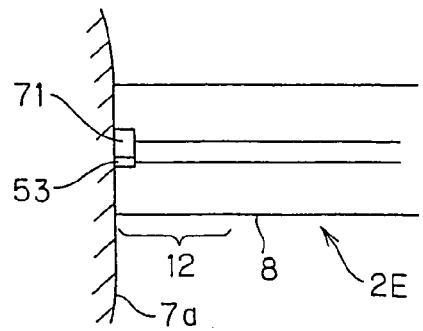
FIGS. 16A and 16B illustrate operation of the endoscopic apparatus of the fourth embodiment that allows observation in the NBI mode.

Thereafter, the surgeon moves the end face of the insert unit 8 to the living mucous membrane 7a as shown in FIG. 16A, thereby putting the end face in contact with the living mucous membrane 7a.

Then, the surface area of the living mucous membrane 7a is heated by the Peltier device 71, and then rises in temperature. As previously described in connection with the first embodiment, the blood flow in the near-surface region of the living mucous membrane 7a increases.

Figure 16B:
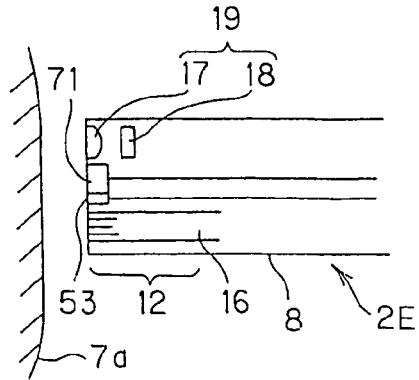

Subsequently, the surgeon then moves the insert unit 8 backward, and observes the living mucous membrane 7a in the NBI observation mode with the end face of the insert unit 8 in close range to the living mucous membrane 7a as shown in FIG. 16B. The fourth embodiment also provides the same advantages as those of the first embodiment. A heating device such as a heater may be used instead of the Peltier device 71.

Next, a first modification of the fourth embodiment is described below. In the fourth embodiment, the Peltier device 71 is heated (warmed) by supplying DC power thereto. The first modification permits the Peltier device 71 to switch between heating and cooling.

By operating the temperature setter 55, the surgeon can set a temperature higher than the temperature of the living mucous membrane 7a or lower than the temperature of the living mucous membrane 7a. In this case, the controller 63 supplies DC power to the Peltier device 71 with the polarity of the DC power of the DC power supply 72 inverted. Thus, the end face of the Peltier device 71 absorbs heat, thereby functioning as cooling means.

Figure 17:
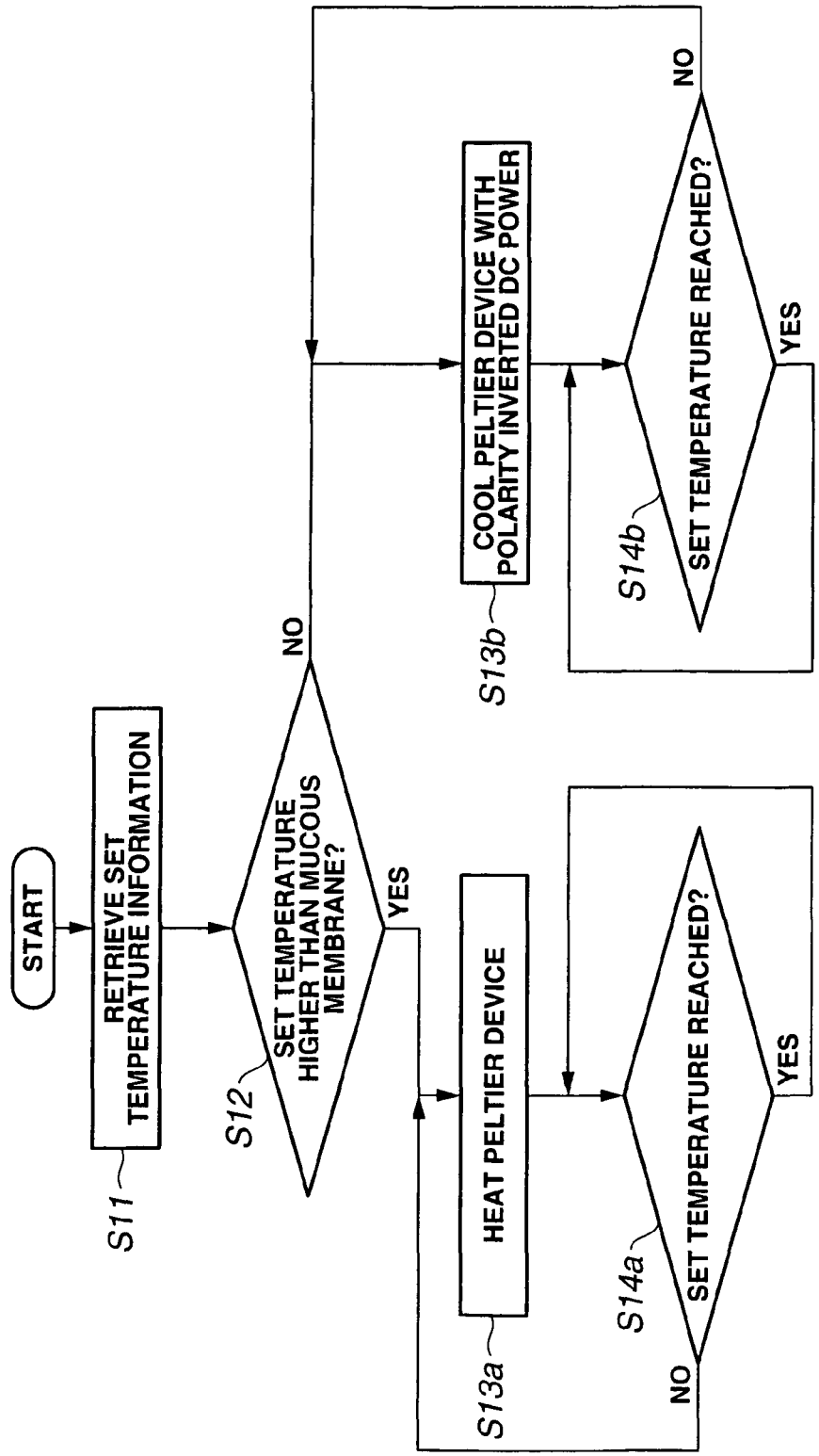
FIG. 17 is a flowchart illustrating operation of a first modification of the fourth embodiment.

Operation of the temperature control of the controller 63 is illustrated in FIG. 17. With the NBI observation mode set, the controller 63 starts a temperature control operation. In step S1, the controller 63 retrieves information regarding temperature set by the temperature setter 55.

In the next step S12, the controller 63 determines whether the set temperature is higher than the temperature of the living mucous membrane 7a.

If it is determined that the set temperature is higher than the temperature of the living mucous membrane 7a, the controller 63 supplies the Peltier device 71 with DC power at a polarity for heating in step S13a, thereby operating the Peltier device 71 with the end face thereof in a heating state.

Meanwhile, if it is determined that the set temperature is lower than the temperature of the living mucous membrane 7a, the controller 63 supplies in step S13b the Peltier device 71 with DC power at a polarity inverted from the polarity for heating, thereby operating the Peltier device 71 with the end face thereof in a cooling state.

Subsequent to step S13a, the controller 63 retrieves in step S14a information regarding the temperature detected by the temperature sensor 53, and then determines whether the detected temperature reaches the set temperature. Heating operation is performed until the detected temperature almost reaches the set temperature.

Subsequent to step S13b, the controller 63 retrieves in step S14b information regarding temperature detected by the temperature sensor 53 and then determines whether the detected temperature reaches the set temperature. Cooling operation is performed until the detected temperature almost reaches the set temperature.

Meanwhile, if the set temperature has been almost reached in step S14a or S14b, the controller 63 continuously performs the temperature determination.

The present modification has the function of providing a change in the blood flow by giving a temperature change to the living mucous membrane 7a not only by heating but also by cooling. In the case of the cooling operation, the blood flow is reduced and the endoscopic image also changes accordingly. The vessels are observed by viewing the change. After the living mucous membrane 7a is cooled by placing the Peltier device 71 into contact therewith, vessel observation may be performed as the blood flow increases while the living mucous membrane 7a is rising in temperature.

Figure 18:
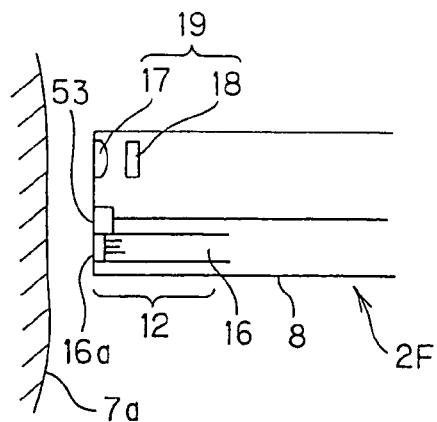
FIG. 18 illustrates the configuration of a distal end portion of an electronic endoscope in accordance with a second modification of the fourth embodiment.

Next, a second modification of the fourth embodiment is described below with reference to FIG. 18. FIG. 18 illustrates a distal end side of an endoscopic apparatus 2F of the second modification. The second modification is without the Peltier device 71 in the electronic endoscope 2E of FIG. 15. The observation apparatus 5 is without the DC power supply. The second modification uses the end face of the light guide 16 as heating means (warming means). The light guide 16 includes at the end face thereof an illumination lens 16a.

In a similar way as previously described with reference to FIG. 16A, the living mucous membrane 7a is heated by putting the end face of the light guide 16 into contact with the living mucous membrane 7a. The living mucous membrane 7a is observed with the blood flow increased. When the light guide 16 is placed in contact with the living mucous membrane 7a, the temperature of the heated living mucous membrane 7a is detected by the temperature sensor 53, and the living mucous membrane 7a is protected from excessive temperature rise above a threshold value.

Fifth Embodiment

Figure 19:
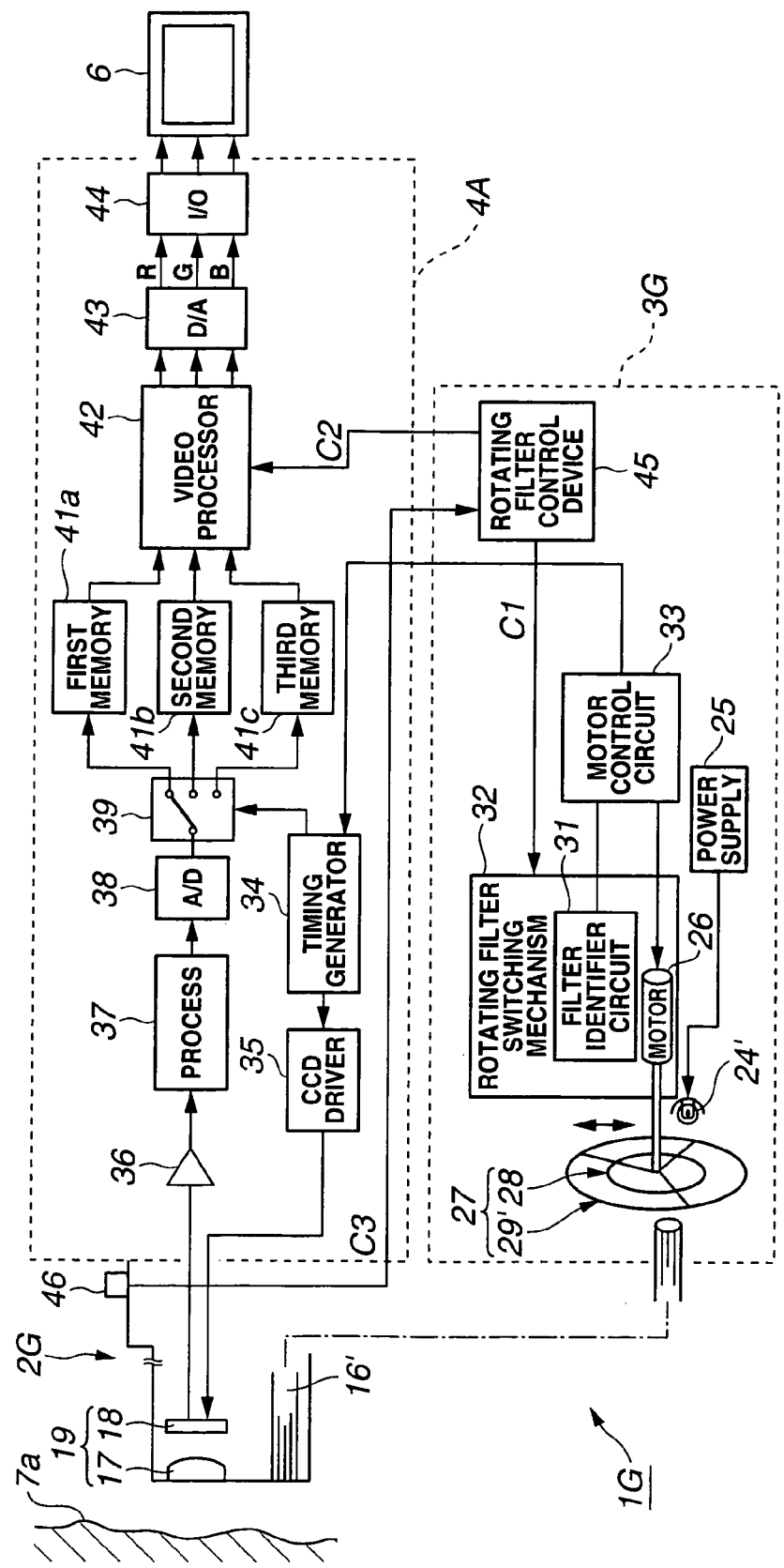
FIG. 19 illustrates the configuration of an endoscopic apparatus in accordance with a fifth embodiment of the present invention.

A fifth embodiment of the present invention is described below with reference to FIG. 19. FIG. 19 illustrates the configuration of an endoscopic apparatus 1G of the fifth embodiment.

Using far-infrared light rays, the fifth embodiment sets in a non-contact manner the blood flow to a state easy to observe.

The endoscopic apparatus 1G of FIG. 19 includes a electronic endoscope 2G without the tubular passage 22 unlike the electronic endoscope 2 of the first embodiment.

Figure 20:
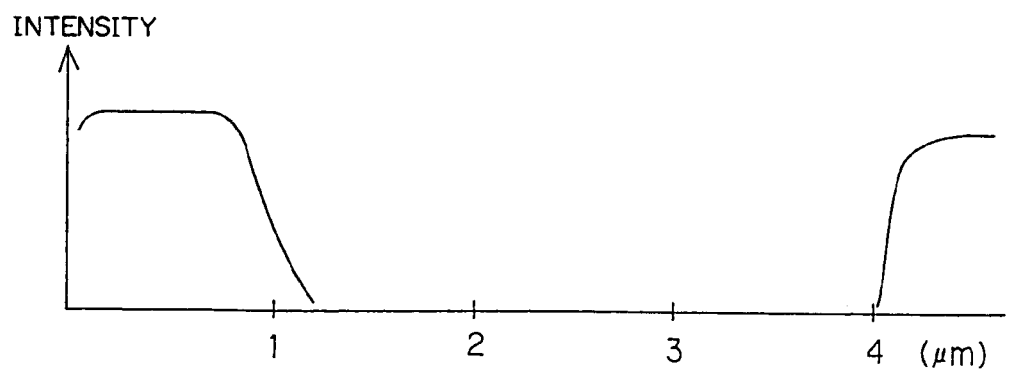
FIG. 20 diagrammatically illustrates spectral characteristics of a light source.
Figure 21:
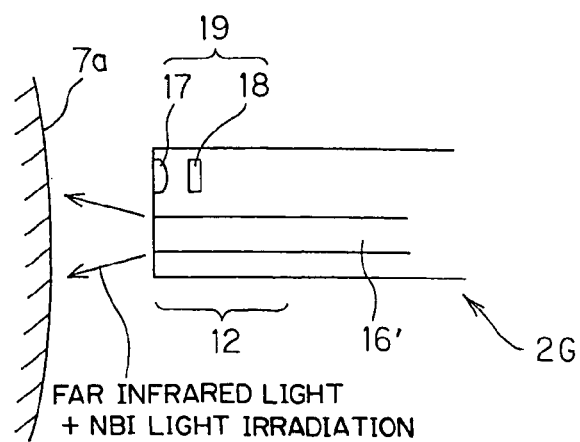
FIG. 21 illustrates a mucous membrane that is observed during the NBI mode.

The observation apparatus 5 of FIG. 19 includes a light source 3G having no thermal medium feeder 23. The light source 3G includes a light source unit 24' that emits light rays in a visible light region of FIG. 20 and a far-infrared region longer than 4 μm. As shown in FIG. 20, no light rays are emitted from within a range from about 1 μm to about 4 μm, but the present invention is not limited to this characteristic.

A second filter set 29' has filter characteristics having the far infrared region of FIG. 20 in addition to the transmittance characteristic of the second filter set 29 of FIG. 4. More specifically, filters R2', G2', and B2' forming the second filter set 29' have the transmittance characteristics that permit the light rays within the far infrared region of FIG. 20 to pass, in addition to the transmittance characteristics of the filters R2, G2, and B2 of FIG. 4, respectively.

A light guide 16' of the electronic endoscope 2G includes far infrared transmission means for transmitting the far infrared light ray in addition to the visible light ray. The light guide 16' may be a hollow structure having an internal surface reflecting light. The light guide 16' irradiates the living mucous membrane 7a with the far infrared light ray transmitted from one end thereof.

The rest of the fifth embodiment remains unchanged from the previously described first embodiment.

Operation of the fifth embodiment is identical to that of the first embodiment in connection with the standard observation mode. With the operation mode switched to the NBI observation mode, the rotating filter control device 45 performs a control process so that the second filter set 29' is aligned with the illumination optical axis as shown in FIG. 19.

Then, since the filters of the second filter set 29' have the transmittance characteristics permitting the far infrared light ray to pass therethrough in addition to the transmittance characteristics of the second filter set 29 of FIG. 4, the observation area is irradiated with the far infrared light ray. More specifically, the observation area is irradiated with the far infrared light ray and the NBI light ray.

Since the far infrared light ray has a property to heat the living organ 7, the observation area irradiated with the far infrared light ray is heated, and the blood flow through the vessels including the capillary vessels increases. Therefore, with the operation mode switched to the NBI observation mode, the capillary vessels are viewed in a state easy to observe. The fifth embodiment provides the same advantages as those of the first embodiment and the other embodiments.

The far infrared light ray may be considered to be warming means for imparting vibration energy to the living mucous membrane 7a (if each molecule forming the living mucous membrane 7a is considered as grating, grating vibration is provided to each grating).

Figure 22:
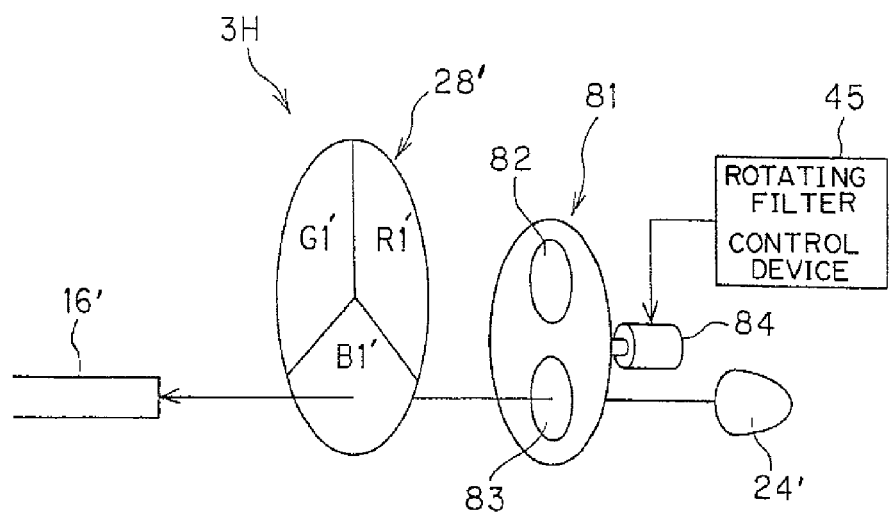
FIG. 22 diagrammatically illustrates the configuration of a light source of a first modification of the fifth embodiment.

Next, a first modification of the fifth embodiment is described below with reference to FIG. 22. FIG. 22 diagrammatically illustrates the configuration of a light source 3H as the first modification.

In the first modification, the rotating filter 27 of FIG. 19 is composed of only a first filter set 28' (represented by reference numeral 28' for simplicity in FIG. 22).

The first filter set 28' is provided with the transmittance characteristics of R1', G1', and B1' permitting the far infrared light ray to pass therethrough in addition to the transmittance characteristics of R1, G1, and B1 of FIG. 4.

A second rotating filter 81 is arranged to face the first filter set 28' in the illumination optical axis. The second rotating filter 81 includes a filter 82 permitting a visible light ray to pass therethrough and a filter 83 permitting an NBI light ray and a far infrared light ray to pass therethrough.

As shown in FIG. 23, the filter 83 has NBI observation filter characteristics permitting light in narrow bands of G2 and B2 therethrough, and characteristics permitting the far infrared light ray therethrough. The NBI observation filter characteristics may be filter characteristics permitting light rays in narrow bands of R2, G2, and B2 therethrough.

The rotating filter control device 45 controls the angle of rotation of a motor 84, thereby controlling the filters that are arranged in the illumination optical axis. During the standard observation mode, the filter 82 permitting the visible light ray to pass therethrough is arranged in the illumination optical axis, and the same operation as described in connection with the first embodiment is performed.

During the NBI observation mode, the rotating filter control device 45 performs the control process, thereby arranging the filter 83 in the illumination optical axis as shown in FIG. 22.

In this case, since the first filter set 28' is rotated, only the far infrared light ray is passed if the R1' filter is arranged in the illumination optical axis. If the G1' filter is arranged in the illumination optical axis, the G2 light ray and the far infrared light ray are passed. If the B1' filter is arranged in the illumination optical axis, the B2 light ray and the far infrared light ray are passed.

Accordingly, the first modification has the operation and advantages similar to those described with reference to FIG. 19.

Figure 24:
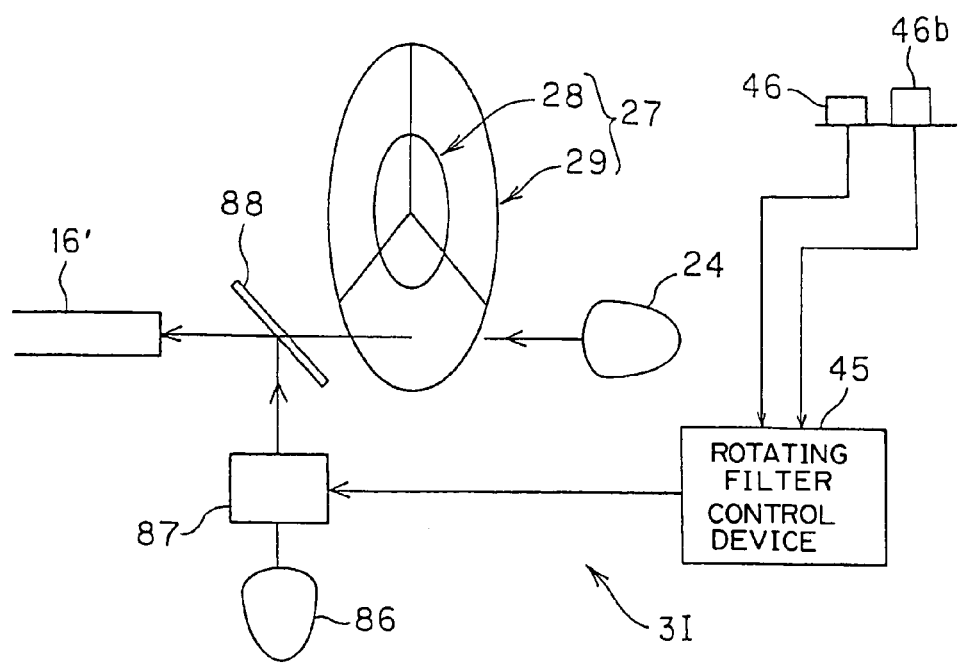
FIG. 24 diagrammatically illustrates the configuration of a light source of a second modification of the fifth embodiment.

FIG. 24 diagrammatically illustrates the configuration of a light source 3I as a second modification. In the light source 3G of FIG. 19, the light source unit 24' includes a lamp having light emission characteristics covering the visible light region and the far infrared light region. In the second modification, the light source 3I includes the (visible light emission) light source unit 24 covering the visible light region and a far infrared light source 86 covering the far infrared light region.

During the standard observation mode, the second modification has the configuration and operation identical to those discussed with reference to FIG. 19. With the operation mode switched to the NBI observation mode, the far infrared light ray from the far infrared light source 86 travels through a shutter 87, and a half-mirror 88 in the illumination optical axis, and then guided to the light guide 16' along with the light ray having passed through the second filter set 29 for NBI observation as shown in FIG. 24.

The half-mirror 88 may be arranged in the illumination optical axis only during the NBI observation mode or may be always arranged in the illumination optical axis.

In the second modification, a pulse irradiation switch 46b is arranged next to the observation mode switch 46 in the electronic endoscope 2G. Operating the pulse irradiation switch 46b, the surgeon irradiates the living mucous membrane 7a with the far infrared light ray thereby pulsed heating the living mucous membrane 7a during the NBI observation mode.

More specifically, operating the pulse irradiation switch 46b, the surgeon sets a pulsed irradiation mode for intermittently irradiating the living mucous membrane 7a with the far infrared light ray. The pulsed irradiation mode provides to the living mucous membrane 7a a blood flow change different from a continuous irradiation mode.

Figure 25:
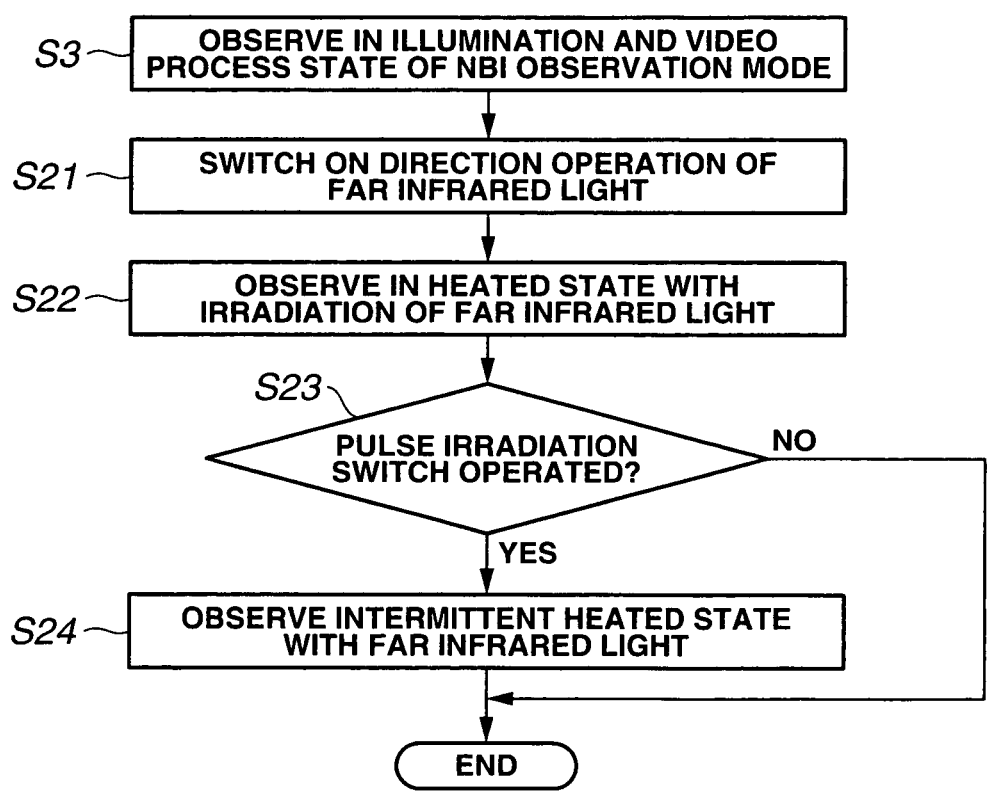
FIG. 25 is a flowchart illustrating operation of the second modification.

FIG. 25 is a flowchart of operation of the NBI observation mode. In response to a switch command to switch to the NBI observation mode, illumination and image processing state for the NBI observation mode are set in step S3 (as in FIG. 6).

The rotating filter control device 45 sets the shutter 87 from off to on in step S21 in response to step S3, thereby allowing the far infrared light ray to enter the light guide 16' together with the NBI observation light ray.

Accordingly, from the end face of the light guide 16' in the electronic endoscope 2G, the NBI observation light ray is directed together with the far infrared light ray to the observation area. In step S22, the observation area is heated by the far infrared light ray and the surgeon can thus observe the observation area with the blood flow increased.

In step S23, the rotating filter control device 45 monitors the operation of the pulse irradiation switch 46b. If the surgeon wants to observe the observation area in pulsed heating, namely, heating alternately on and off, the surgeon operates the pulse irradiation switch 46b.

In step S24, the rotating filter control device 45 turns on and off the shutter 87 at periodic intervals. The surgeon can thus observe a change in the blood flow by pulsed heating with the far infrared light ray.

In accordance with the second modification, the surgeon observes the capillary vessels by selecting between the continuous heating mode and the pulsed heating mode. The rest of the second modification remains unchanged from the fifth embodiment and has similar advantages as those of the fifth embodiment.

In a modification to the arrangement of FIG. 24, the electronic endoscope 2G includes the light guide 16 instead of the light guide 16' and an separately arranged far infrared light transmitter for transmitting the far infrared light ray.

When the NBI observation mode is set, the far infrared light ray from the far infrared light source 86 may be incident on the proximal end of the far infrared light transmitter. The far infrared light ray output from the distal end of the far infrared light transmitter may be then directed to the living mucous membrane 7a. In this case, the far infrared light transmitter may be integrally formed to the electronic endoscope 2G or may be detachably mounted in the channel 21.

A temperature sensor 94 to be described in connection with a sixth embodiment, not arranged in the electronic endoscope 2G of FIG. 19, may be used. The temperature of the living mucous membrane 7a may be detected in a non-contact fashion using the temperature sensor 94 and then monitored.

Sixth Embodiment

Figure 26:
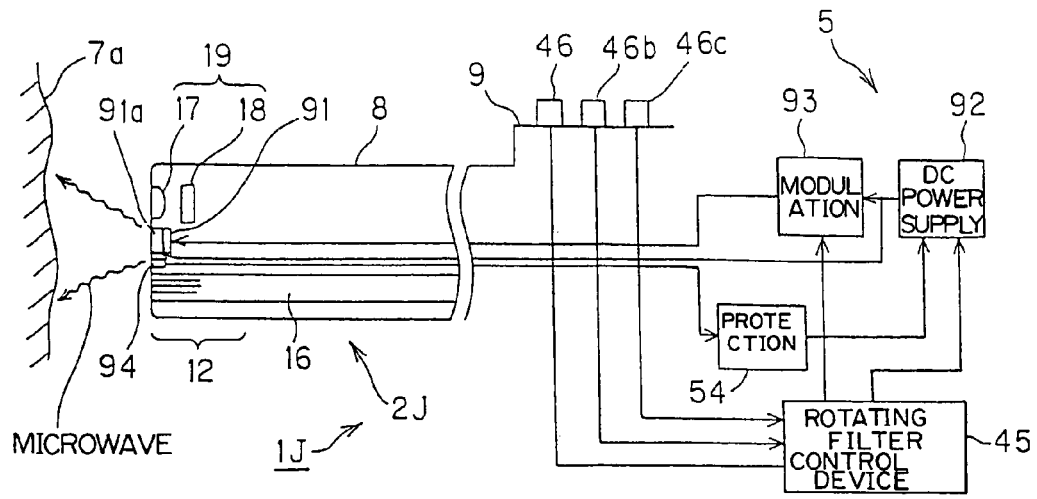
FIG. 26 diagrammatically illustrates the configuration of a major portion of an endoscopic apparatus in accordance with a sixth embodiment of the present invention.

A sixth embodiment is described below with reference to FIG. 26. FIG. 26 illustrates the configuration of a major portion of an endoscopic apparatus 1J in accordance with the sixth embodiment of the present invention.

When the NBI observation mode is set in the fifth embodiment, the living mucous membrane 7a is irradiated with the far infrared light ray. In the sixth embodiment, the living mucous membrane 7a is irradiated with a microwave rather than the far infrared light ray.

An electronic endoscope 2J of the sixth embodiment includes a microwave irradiation device 91 for directing a microwave arranged at the end of the electronic endoscope 2G of FIG. 19.

The microwave irradiation device 91 is supplied with DC power or pulsed power from the DC power supply 92 in the observation apparatus 5 via a pulse modulation circuit (simply referred to as "modulation" in FIG. 26) 93. The microwave irradiation device 91 thus generates a microwave continuously or in a pulsed form, thereby directing the microwave to the observation area such as the living mucous membrane 7a.

With the microwave directed, water molecules in the living mucous membrane 7a in the observation area absorb vibration energy of an electromagnetic wave, i.e., the microwave, and are thus heated. Heat is also transferred to molecules, other than the water molecules, surrounding the water molecules. These molecules are also heated.

The temperature sensor 94 for detecting radiation temperature is arranged next to the microwave irradiation device 91. The temperature sensor 94 detects the temperature of the observation area and then outputs the detected temperature to the protective circuit 54.

The temperature sensor is composed of a thermopile, and detects the temperature of the observation area in a non-contact fashion. The temperature sensor is thus used to prevent the observation area from being heated at a predetermined temperature value or higher.

The protective circuit 54 switches off the DC power supply 92 when the temperature detected by the temperature sensor 94 rises above the threshold value.

The observation mode switch 46 is connected to the rotating filter control device 45. When the observation mode switch 46 issues a switch command to switch to the NBI observation mode, the rotating filter control device 45 activates the DC power supply 92. In this case, the DC power supply 92 supplies DC power to the microwave irradiation device 91 via the pulse modulator circuit 93.

When the pulse irradiation switch 46b is operated, the rotating filter control device 45 controls to operate the pulse modulator circuit 93 to supply pulsed DC power to the microwave irradiation device 91.

A radiation angle changing device 91a for switching a radiation angle of the microwave between a narrow angle and a wide angle is arranged at the front of the microwave irradiation device 91. The surgeon operates a radiation angle changing switch 46c to set the radiation angle of the microwave to a narrow angle or a wide angle depending on an observation distance to the living mucous membrane 7a.

The rotating filter control device 45, receiving an operation signal of the radiation angle changing switch 46c, controls the radiation angle changing device 91a by switching on and off DC power from the DC power supply 92. The DC power is normally cut off, and in this state, the radiation angle changing device 91a causes the microwave to be directed at a narrow angle.

The radiation angle changing device 91a is, for example, a horn type waveguide that guides the microwave, generated by a semiconductor device, and radiates the microwave from an end opening. A horn portion of the waveguide is made of a shape-memory metal. The horn portion, when supplied with DC power, rises in temperature. With a shape-memory function of a high-temperature phase side of the shape-memory metal, the metal in a high-temperature phase side changes to a different shape in an opening angle (to a wider angle) different from a low-temperature phase side of the metal. The light source of the sixth embodiment, although not shown in FIG. 26, is identical in configuration to the light source 3 of the first embodiment, for example.

Operation of the sixth embodiment is described below. The operation of the sixth embodiment remains unchanged from that of the first embodiment during the standard observation mode.

Figure 27:
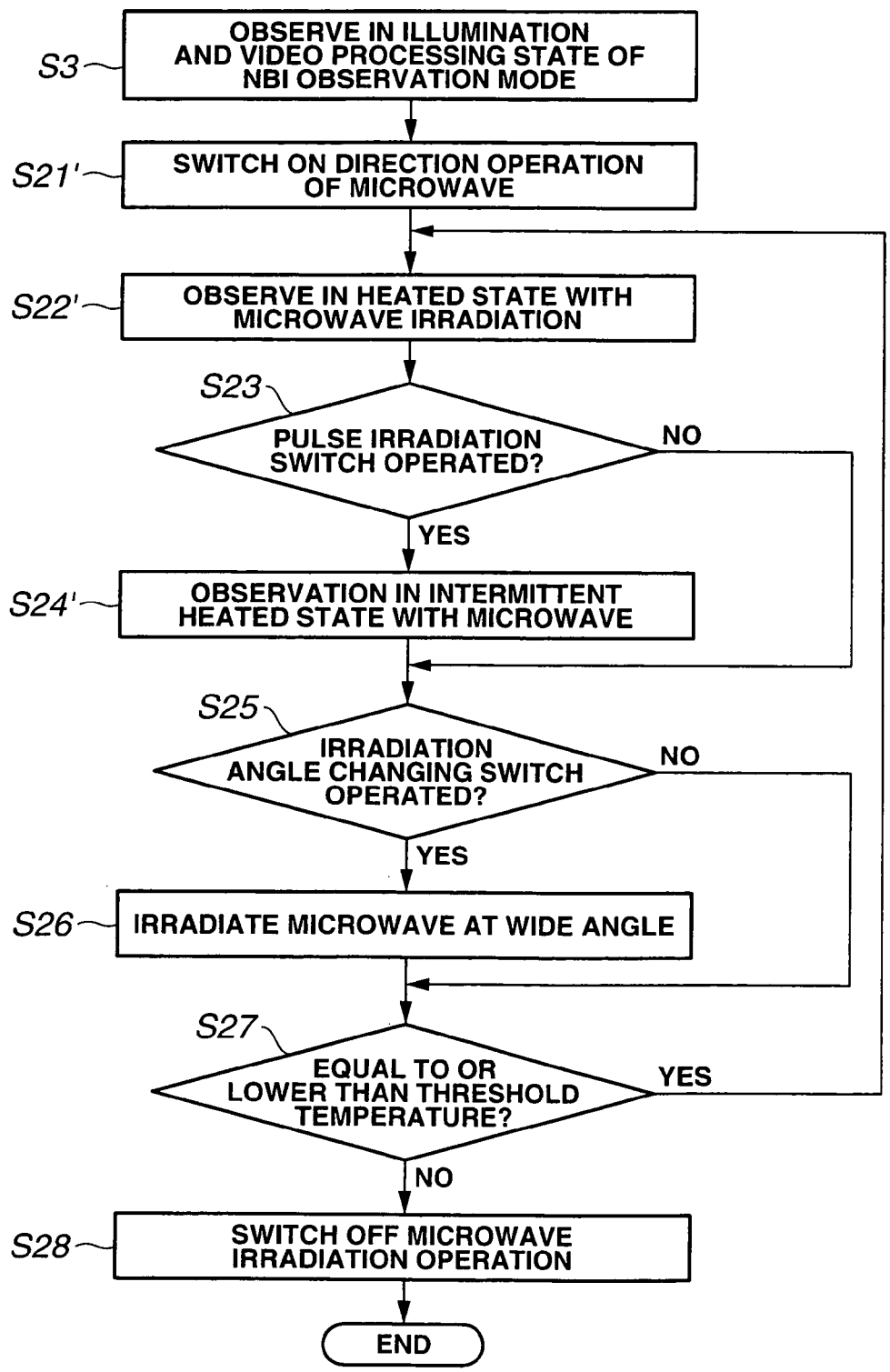
FIG. 27 is a flowchart illustrating operation of the sixth embodiment.

With the operation mode switched to the NBI observation mode, the sixth embodiment operates as described in a flowchart of FIG. 27. In steps S3 to S24' in FIG. 27, the microwave is used instead of the far infrared light ray used as described with reference to corresponding steps in FIG. 25. Steps in FIG. 27 modified from the corresponding steps in FIG. 25 are thus marked with the sign (').

Subsequent to step S24' in the sixth embodiment, the rotating filter control device 45 monitors in step S25 whether the radiation angle changing switch 46c is operated. If the radiation angle changing switch 46c is not operated, the microwave irradiation device 91 emits the microwave at a narrow angle.

The surgeon typically observes the living mucous membrane 7a with the distal end portion 12 in the electronic endoscope 2J placed in close range with the living mucous membrane 7a. In contrast, to observe the living mucous membrane 7a to view a wide area at a longer range than an ordinary observation distance, the surgeon may operate the radiation angle changing switch 46c.

In this case, DC power is supplied to the radiation angle changing device 91a in step S26, and the radiation angle of the microwave is switched to a wide angle. And, a wide area of the living mucous membrane 7a is irradiated with the microwave. That is, depending on the observation area of the living mucous membrane 7a, a heated area is also changed. The microwave irradiation device 91 increases the blood flow in the vessels such as the capillary vessels in the heated area, thereby setting the living mucous membrane 7a in a state easy to view.

In step S27, the protective circuit 54 monitors whether the temperature detected by the temperature sensor 94 is equal to or lower than the threshold value. If the detected temperature is equal to or lower than the threshold value, processing returns to step S22'. In this case, the microwave irradiation device 91 continues to irradiate the living mucous membrane 7a with the microwave.

Meanwhile, if the temperature detected by the protective circuit 54 rises above the threshold value, the DC power supply 92 is switched off in step S28, thereby stopping microwave irradiation.

The energy level of the microwave directed in a pulse form with the pulse irradiation switch 46b operated is set to a higher value than when the microwave is continuously directed. This increases the effectiveness of the function of increasing the blood flow with time. In this way, the capillary vessels or the like, become easier to observe.

The sixth embodiment provides the same advantages as those of the second modification of the fifth embodiment. Furthermore, a range where the living mucous membrane 7a is heated (in other words, a range where the blood flow changes) can be modified. The temperature sensor 94 of FIG. 26 may be included in another embodiment so that the temperature of the living mucous membrane 7a being heated is detected in a non-contact fashion to prevent the living mucous membrane 7a from being heated at a predetermined temperature or higher.

Figure 28:
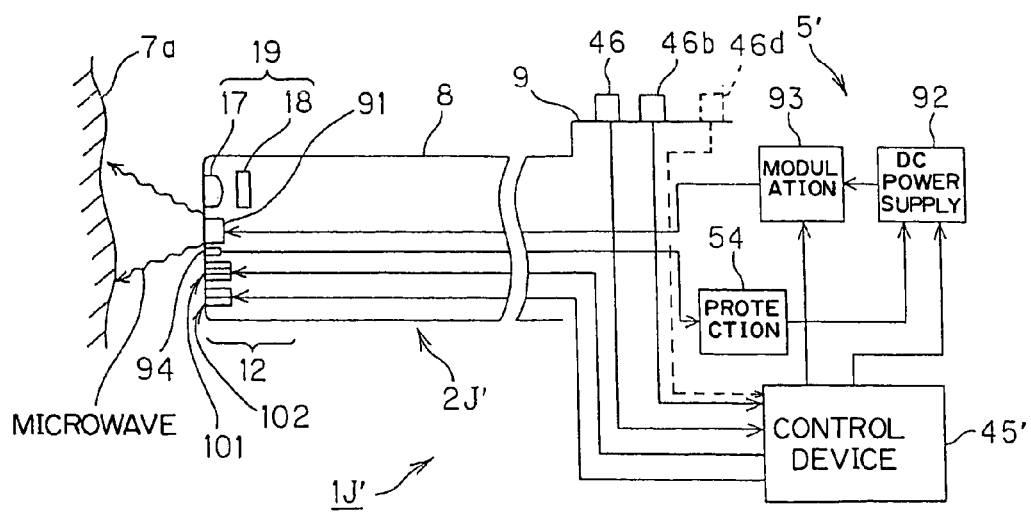
FIG. 28 diagrammatically illustrates the configuration of a major portion of the endoscopic apparatus as a modification of the sixth embodiment of the present invention.

FIG. 28 illustrates the configuration of a major portion of an endoscopic apparatus 1J' as a modification.

The endoscopic apparatus 1J' includes an electronic endoscope 2J' and an observation apparatus 5'. The electronic endoscope 2J' is identical to the electronic endoscope 2J except that no light guide 16 is contained and that three color light emitting diodes (LED) 101 and two color light emitting diodes LED 102 are arranged at the distal end portion 12.

During the standard observation mode, under the control of the rotating filter control device 45', the three color LED 101 emits light rays and during the NBI observation mode, the two color LED 102 emits light rays.

The three color LED 101 successively emits frame-sequential illumination light rays by the first filter set 28, namely, R1, G1, and B1 light rays, and the two color LED 102 successively emits the illumination light rays by the second filter set 29, namely, G2 and B2 light rays of FIG. 23.

The rotating filter control device 45' operates in almost the same way as the rotating filter control device 45. More specifically, the rotating filter control device, 45' does not perform a rotating filter switching control process, but performs a switching control process for switching the illumination light rays in the same way as when the rotating filter is switched. The rotating filter control device 45' performs a switching control on the video processor 42 although such a control process is not identified in FIG. 28.

In this modification, the microwave irradiation device 91 is without the radiation angle changing device 91a. Accordingly, the electronic endoscope 2J' is without the radiation angle changing switch 46c.

The modification provides operations and advantages substantially identical to those of the endoscopic apparatus 1J' of FIG. 26 except the operation of changing the radiation angle of the microwave.

In the sixth embodiment, the living mucous membrane is irradiated with the microwave. Alternatively, the living mucous membrane may be irradiated with ultrasonic wave, such as ultrasonic microwave.

Seventh Embodiment

Figure 29:
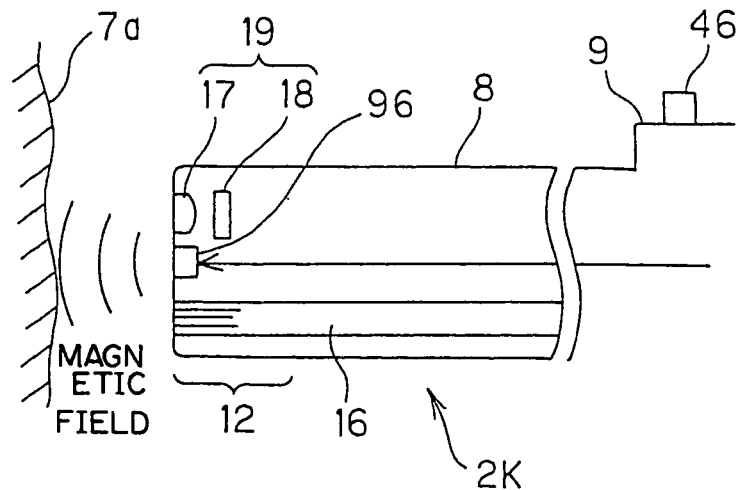
FIG. 29 illustrates the configuration of a distal end portion of an endoscopic apparatus in accordance with a seventh embodiment of the present invention.

A seventh embodiment of the present invention is described below with reference to FIG. 29. FIG. 29 illustrates the configuration of a distal end portion of an electronic endoscope 2K in accordance with the seventh embodiment of the present invention. The seventh embodiment includes a magnetic coil 96 for applying magnetic energy instead of the microwave irradiation device 91 in the sixth embodiment.

In this case, the temperature sensor 94 is not included herein. During the NBI observation mode, the living mucous membrane 7a is irradiated with magnetic energy generated by the magnetic coil 96. The seventh embodiment increases the blood flow and facilitates observation of the capillary vessels or the like, by directing the magnetic energy to the living mucous membrane 7a.

Figure 30:
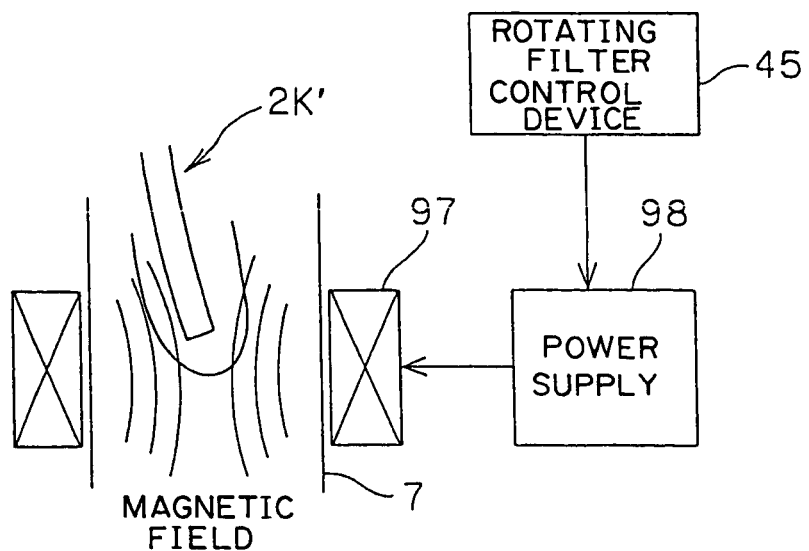
FIG. 30 illustrates the configuration of a major portion of a modification of the seventh embodiment of the present invention.

A modification of the seventh embodiment includes an external magnetic coil 97 arranged external to the living organ 7 as shown in FIG. 30. The external magnetic coil 97, powered by a power supply 98, directs magnetic energy to the living organ 7. In this case, an electronic endoscope 2K' to be inserted into the living organ 7 is without the magnetic coil 96 of the electronic endoscope 2K of FIG. 29. The power supply 98 is controlled by the rotating filter control device 45.

As shown in FIG. 30, the external magnetic coil 97 also directs magnetic energy to a portion of the living organ 7 observed by the electronic endoscope 2K'.

During the NBI observation mode in the modification, magnetic energy is directed to the observation area observed by the electronic endoscope 2K' from the outside, and vessels such as capillary vessels are observed with the blood flow therewithin increased.

In the modification of FIG. 30, the external magnetic coil 97 arranged external to the living organ 7 directs the generated magnetic energy to the living organ 7. The present invention is not limited to this arrangement. For example, magnetic energy generating means such as the magnetic coil 96 may be arranged external to the electronic endoscope 2K'.

Eighth Embodiment

Figure 31:
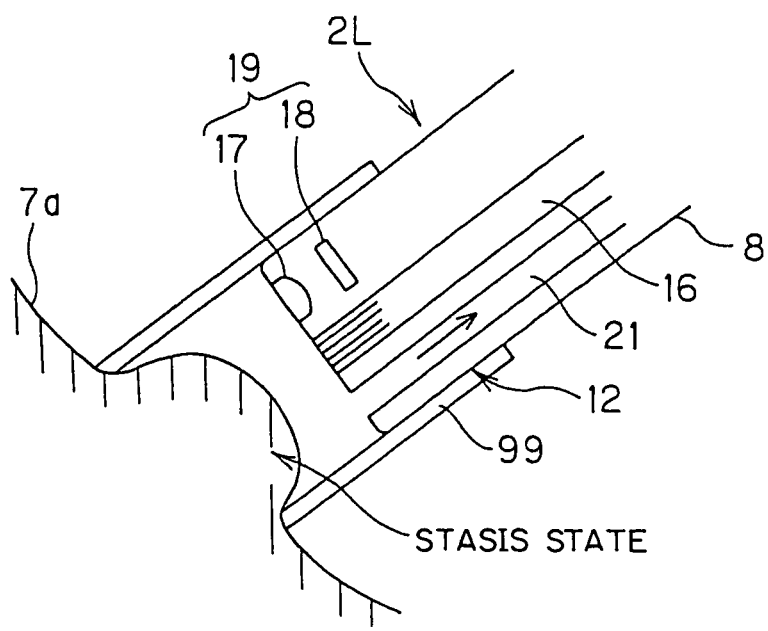
FIG. 31 diagrammatically illustrates the configuration of a distal end portion of an endoscopic apparatus in accordance with an eight embodiment of the present invention.

An eighth embodiment of the present invention is described below with reference to FIG. 31. FIG. 31 illustrates the configuration of a distal end portion of an endoscopic apparatus 2L in accordance with the eighth embodiment of the present invention. In the eighth embodiment, a cap 99 is loaded to the distal end portion 12 in one of the electronic endoscope 2K' of FIG. 30 and the electronic endoscope 2A of FIG. 11.

During the NBI observation mode, the endoscopic apparatus 2L suctions the surface of the living mucous membrane 7a via the channel 21. As shown in FIG. 31, the vessels in the portion of the living mucous membrane 7a suctioned into the cap 99 are forced into stasis state for easy observation.

With the eighth embodiment, vessels such as capillary vessels set to the easy-to-observe state thereof are observed using an existing electronic endoscope.

In addition to means and methods of the above-described embodiments for changing the blood flow, the present invention also includes means and methods for changing the blood flow in vessels such as capillary vessels by providing a stimulation to the living mucous membrane 7a. For example, the living mucous membrane 7a is pressed and then released. Subsequent to the removal of the pressure, the living mucous membrane 7a is reddened. Taking advantage of this phenomenon, observation may be performed in the NBI observation mode after the removal of the pressure.

The present invention also includes a mechanism in which the position of a body is changed in response to the switching of the operation mode to the NBI observation mode. With the position of the body changed, the blood flow is changed taking advantage that blood tends to easily flow in the direction of gravity. The observation of the vessels such as the capillary vessels and the blood flow through the vessels is thus facilitated during the NBI observation mode.

In accordance with the above-referenced embodiments, a blood flow changer changes the blood flow through vessels including capillary vessels at the near-surface layer of the living organ in the body cavity, thereby facilitating observation of the vessel and the blood flow therethrough.

A different embodiment may be constructed by combining parts of the above-referenced embodiments. For example, the heating device such as the Peltier device 71 of FIG. 15 and the microwave irradiation device 91 of FIG. 26 may be mounted on a wire or a tube inserted through the channel 21 instead of being mounted on the distal end portion 12 of the insert unit 8.

The present invention is not limited to the arrangement in which the blood flow changing means for changing the blood flow is integrated with the endoscope. The present invention also includes the arrangement in which the blood flow changing means is detachably mounted on the endoscope.

When the operation mode is switched from the standard observation mode to the NBI observation mode in the above-referenced embodiments, the blood flow changing means for increasing the blood flow is operatively driven. The present invention is not limited to the arrangement in which the blood flow increasing is timed to the observation mode switching. The surgeon may turn on and off the blood flow changing means.

A switch 46d for issuing a command to turn on and off the microwave irradiation device 91 forming the blood flow changing means may be arranged in the operation unit 9 of FIG. 28 (as represented by broken line in FIG. 28).

The operation signal of the switch 46d is input to the control device 45'. The control device 45' switches on and off power to be supplied to the microwave irradiation device 91 in response to the on/off operation signal (for starting and stopping the supply of power).

This arrangement may be incorporated in another embodiment. For example, a switch 46d is arranged in the first embodiment of FIG. 2, and in response to the on/off operation signal of the switch 46d, the heating power from the heater power supply 51 to the heater 50 is switched on and off and the pump 48 is switched on and off.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscopic apparatus for observing an inside of a body cavity, comprising:
    an endoscope including an operation unit, an insert section, extending from the operation unit toward a distal end, to be inserted into the body cavity, an illumination window for directing illumination light therethrough and an observation window for observing an illuminated internal portion of the body cavity, arranged at a distal end portion of the insert section;
    a light source configured to emit visible-light illumination light and narrow-band illumination light through the illumination window;
    an observation mode switch for selectively outputting the visible-light illumination light and the narrow-band illumination light set in at least a wavelength region of blue;
    a blood flow changing section formed at the distal end portion independently of the visible-light illumination light and the narrow-band illumination light outputted through the illumination window, for increasing a blood flow of blood flowing through a vessel by thermally heating the blood in a near-surface region of a living organ inside the body cavity; and
    a control device configured to automatically turn on the blood flow changing section to increase the blood flow by switching from the visible-light illumination light to the narrow-band illumination light in response to actuation of the observation mode switch, and configured to automatically turn off the blood flow changing section halting the increase in the blood flow by switching from the narrow-band illumination light to the visible-light illumination light in response to actuation of the observation mode switch.

2. The endoscopic apparatus according to claim 1, wherein the blood flow changing section is mounted on the endoscope detachably or in an integrally fixed manner as a unitary body.

3. The endoscopic apparatus according to claim 2, wherein the blood flow changing section is detachably mounted on a channel of the endoscope.

4. The endoscopic apparatus according to claim 1, wherein the light source further comprises a far-infrared generator for generating far infrared light.

5. The endoscopic apparatus according to claim 4, wherein the endoscope comprises a far infrared light transmitter for transmitting the far infrared light generated by the far-infrared generator to the distal end portion thereof, and a far-infrared light irradiator for irradiating a surface of the living organ in the body cavity with the far infrared light from the distal end portion of the far-infrared light transmitter.

6. The endoscopic apparatus according to claim 1, wherein the blood flow changing section comprises a medium sprayer for spraying a warmed medium onto a surface of the living organ in the body cavity.

7. The endoscopic apparatus according to claim 6, further comprising a temperature setter for setting a temperature to which the medium to be sprayed onto the surface of the living organ in the body cavity is warmed.

8. The endoscopic apparatus according to claim 4, wherein a surface of the living organ in the body cavity is irradiated with the far infrared light together with the narrow-band illumination light in response to the operation of the observation mode switch.

9. The endoscopic apparatus according to claim 4, wherein the light source selectively supplies the far infrared light and the visible-light illumination light to the endoscope by moving a filter that allows the far infrared light to pass therethrough.

10. The endoscopic apparatus according to claim 1, comprising a temperature sensor for detecting a temperature of a surface of the living organ in which the blood flow changing section provides a change in the blood flow.

11. The endoscopic apparatus according to claim 10, comprising a temperature monitor for monitoring whether the temperature detected by the temperature sensor rises above a predetermined temperature.

12. The endoscopic apparatus according to claim 11, wherein the temperature monitor stops the operation of the blood flow changing section for blood flow change when the detected temperature rises above the predetermined temperature.

13. The endoscopic apparatus according to claim 1, wherein the blood flow changing section includes a pulsed-heating section for intermittently heating a surface region of the living organ inside the body cavity.

14. The endoscopic apparatus according to claim 13, wherein the pulsed-heating section is formed with a pulsed-irradiation section for intermittently irradiating far-infrared light rays.

15. The endoscope apparatus according to claim 1, wherein the blood flow changing section includes a vibration energy providing device for heating the blood in the near-surface region of the living organ inside the body cavity by providing vibration energy.

* * * * *